US012258606B2

(12) United States Patent
Rice et al.

(10) Patent No.: US 12,258,606 B2
(45) Date of Patent: *Mar. 25, 2025

(54) LIMITING YEAST-PRODUCED TREHALOSE IN FERMENTATION

(71) Applicant: Lallemand Hungary Liquidity Management LLC, Budapest (HU)

(72) Inventors: Charles F. Rice, Plainfield, NH (US); Ryan Skinner, Bethel, VT (US); Trisha Barrett, Bradford, VT (US); Aaron Argyros, Lebanan, NH (US)

(73) Assignee: DANSTAR FERMENT AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/183,669

(22) Filed: Mar. 14, 2023

(65) Prior Publication Data

US 2023/0265463 A1 Aug. 24, 2023

Related U.S. Application Data

(63) Continuation of application No. 17/170,529, filed on Feb. 8, 2021, now Pat. No. 11,634,734, which is a continuation of application No. 16/776,389, filed on Jan. 29, 2020, now Pat. No. 10,947,568, which is a continuation of application No. 15/773,139, filed as application No. PCT/IB2016/056658 on Nov. 4, 2016, now Pat. No. 10,570,421.

(60) Provisional application No. 62/251,885, filed on Nov. 6, 2015.

(51) Int. Cl.
| | |
|---|---|
| *C12P 7/10* | (2006.01) |
| *C12N 1/18* | (2006.01) |
| *C12N 9/24* | (2006.01) |
| *C12N 15/81* | (2006.01) |
| *C12P 7/20* | (2006.01) |
| *C12P 19/12* | (2006.01) |

(52) U.S. Cl.
CPC ............. *C12P 7/10* (2013.01); *C12N 1/18* (2013.01); *C12N 9/2402* (2013.01); *C12N 15/81* (2013.01); *C12P 7/20* (2013.01); *C12Y 302/01028* (2013.01); *C12P 19/12* (2013.01); *Y02E 50/10* (2013.01)

(58) Field of Classification Search
CPC .............. C12P 7/10; C12N 1/18; C12N 15/81
See application file for complete search history.

(56) References Cited

U.S. PATENT DOCUMENTS

| | | | |
|---|---|---|---|
| 10,570,421 B2 * | 2/2020 | Rice | C12P 7/10 |
| 10,947,568 B2 * | 3/2021 | Rice | C12P 7/10 |
| 11,198,881 B2 | 12/2021 | Argyros et al. | |
| 2018/0320203 A1 | 11/2018 | Rice et al. | |

FOREIGN PATENT DOCUMENTS

| | | |
|---|---|---|
| WO | 2011/153516 A2 | 12/2011 |
| WO | 2015/023989 A1 | 2/2015 |
| WO | 2015/065871 A1 | 5/2015 |
| WO | 2015/065978 A1 | 5/2015 |
| WO | 2015/148272 A1 | 10/2015 |

OTHER PUBLICATIONS

Amaral et al., "Molecular cloning of the neutral trehalase gene from *Kluyveromyces lactis* and the distinction between neutral and acid trehalases," Arch Microbiol. Apr. 1997;167(4):202-8.
An et al., "Enhanced thermotolerance for ethanol fermentation of *Saccharomyces cerevisiae* strain by overexpression of the gene coding for trehalose-6-phosphate synthase," Biotechnol Lett. 33.7 (2011): 1367-1374.
Bell et al., "Composition and Functional Analysis of the *Saccharomyces cerevisiae* Trehalose Synthase Complex," Journal of Bio Chem. 11 (1998): 33311-33319.
Cao et al., "Expression of TPS1 gene from *Saccharomycopsis fibuligera* A11 in *Saccharomyces* sp. W0 enhances trehalose accumulation, ethanol tolerance, and ethanol production," Mol Biotechnol 56.1 (2014): 72-78.
De Virgilio et al., "Disruption of *TPS2*, the gene encoding the 100-kDa subunit of the trehalose-6-phosphate synthase/phosphatase complex in *Saccharomyces cerevisiae*, causes accumulation of trehalose-6-phosphate and loss of trehalose-6-phosphate phosphatase activity," Eur J Biochem. Mar. 1, 1993;212(2):315-23.
Elbein et al., "New insights on trehalose: a multifunctional molecule," Glycobiology. 13.4 (2003): 17R-27R.
Elliott et al., Synergy between trehalose and Hsp104 for thermotolerance in *Saccharomyces cerevisiae*. Genetics. Nov. 1996;144(3):923-33.
Frison et al., "The *Arabidopsis thaliana* trehalase is a plasma membrane-bound enzyme with extracellular activity," FEBS Lett. Aug. 21, 2007;581(21):4010-6.
Ge et al., "Improve carbon metabolic flux in *Saccharomyces cerevisiae* at high temperature by overexpressed *TSL1* gene," J Ind Microbiol Biotechnol. 40 (2013): 345-352.
Giffen, New Insights into fermentation drop samples: The real story of total residual sugars. Fuel Ethanol Workshop and Expo. Minneapolis, MN. Jun. 5, 2012, 13 pages.
Guo et al., "Minimization of glycerol synthesis in industrial ethanol yeast without influencing its fermentation performance," Metabol Eng 13.1 (2011): 49-59.

(Continued)

*Primary Examiner* — Tekchand Saidha
(74) *Attorney, Agent, or Firm* — Seed IP Law Group LLP

(57) ABSTRACT

The present disclosure relates to recombinant yeast host cells having (i) a first genetic modification for reducing the production of one or more native enzymes that function to produce glycerol or regulating glycerol synthesis and/or allowing the production of an heterologous glucoamylase and (ii) a second genetic modification for reducing the production of one or more native enzymes that function to produce trehalose or regulating trehalose synthesis and/or allowing the expression of an heterologous trehalase. The recombinant yeast host cells can be used to limit the production of (yeast-produced) trehalose (particularly extracellular trehalose) during fermentation and, in some embodiments, can increase the production of a fermentation product (such as, for example, ethanol).

17 Claims, 7 Drawing Sheets

Specification includes a Sequence Listing.

(56) References Cited

OTHER PUBLICATIONS

Liu et al., "Expression, purification, and characterization of recombinant *Metarhizium anisopliae* acid trehalase in *Pichia pastoris*," Protein Expr Purif. Jul. 2007;54(1):66-72.
Singer et al., "Thermotolerance in *Saccharomyces cerevisiae*: the Yin and Yang of trehalose," Trends Biotechnol. 16.11 (1998): 460-468.
Thevelein et al., "Trehalose synthase: guard to the gate of glycolysis in yeast?" Trends Biochem Sci 20.1 (1995): 3-10.
Van Dijck et al., "Disruption of the *Candida albicans TPS2* gene encoding trehalose-6-phosphate phosphatase decreases infectivity without affecting hypha formation," Infect Immun. Apr. 2002;70(4):1772-82.
Zilli et al., "Secretion of the acid trehalase encoded by the *CgATH1* gene allows trehalose fermentation by *Candida glabrata*," Microbiol Res. Oct. 2015; 179:12-9.

\* cited by examiner

SEQUENCE LISTING

```
Sequence total quantity: 60
SEQ ID NO: 1                   moltype = AA  length = 1072
FEATURE                        Location/Qualifiers
source                         1..1072
                               mol_type = protein
                               organism = Aspergillus fumigatus
SEQUENCE: 1
MLSQNLATWV SLLACLPAAI GLPNNNDRVA RSLKRHGGHG HKQVDTNSSH VYKTRFPGVT   60
WDDDHWLLST TTLDQGHYQS RGSIANGYLG INVASVGPFF ELDVPVSGDV INGWPLYSRR  120
QTFATIAGFF DYQPTTNGSN FPWLNQYGGE SVISGIPHWS GLILDLGDGN YLDATVDNKT  180
ITDFRSTYDF KSGVLSWSYT WTPKCNKGSF NITYRLFAHK LHVNQAVVDM EITPSQGSEA  240
TVVNVIDGFS AVRTDFVESG QDNGALFSAV RPWGISNVTA YVYTNLTASA GVDLTSRALV  300
NDKPYVHSNE SSIAQAVDVK FRANETVRIT KFVGAASSDA FPNPQQTAKQ AVSAAMGAGY  360
MGSLQSHVEE WASILLDGSV DSFVDPATGK LPDDDHILNS QIIAVANTYY LLQNTVGKNA  420
IKAVSGAPVN VDSISVGGLT SDSYAGLVFW DADVWMQPGL VASHPEAAQR VTNYRTKLYP  480
QALENINTAF TSSKNRTTFS PSAAIYPWTS GRFGNCTGTG PCWDYQYHLN GDIGLSLMYQ  540
WIASGDTKTF REQHFPIYDS VATMYSNIVQ RNGSSWTLTN MTDPDEYANH IDAGGFTMPL  600
ISETLSYANS FRKQFGLEQN ETWTEISENV LLIREDGVTL EYTTMNGTAV VKQADIVLVT  660
YPLVVDNNYT AQHALNDLDY YANQQSPDGP AMTWAIFAIT ANDVSPSGCS AYTYHQDSYD  720
PYMRAPFYQL SEQMIDDAGI NGGTHPAYPF LTGHGGANQV VLMGYLGLRL LPDDAIHIDP  780
NLPPQVSNLK YRTFYWRGWP ISSSSNRTHT TISRAANLAP LDTADSRFAN ASIPVLVGDP  840
SNSTAYRLPV TAPLVVPNRQ IGFNNTIPGN MVQCRPVYSP NDYAPGQFPI AAVDGATSTK  900
WRPSTANMSS LTVALADVEI NSKVSGFHFN WWQAPPVNAT VIFHDEMLED PVAAMSSSHG  960
NSRYRVVTTL TNIEQSQPYD AQSTDNNEVV LNTGNTTDVS LSQTVHTSRY ATLLISGNQA 1020
GGEEGATVAE WAILGESKGS SSGHGNNKRR LDVRAAAALS ALNDRRYRQF NA         1072

SEQ ID NO: 2                   moltype = AA  length = 1054
FEATURE                        Location/Qualifiers
source                         1..1054
                               mol_type = protein
                               organism = Aspergillus nidulans
SEQUENCE: 2
MRFKSVFTLL PLLAQLPSGG ASLPNNHGRV ENCVRNHDGI HKFRHSNNTY QSMFPGVTWD   60
EDQWVLTTSS LDQGHYQSRG SVANGYIGIS VSSVGPFFEL DLPVAGDVIN GWPLYSRRQS  120
FATISGFFDI QAETNGSNFP WMNQYGGESV ISGVPHWSGL ILDLGDDDYL DSTVDNVTLS  180
DFKSSYDFKA GVLSWSYTWT PAGDKGSYAI TYRLFANKLN VNQAVVDMEI TPSQDGHATI  240
VNVLDGYSAV RTDFVESQED DGAIYSAVRP WGIPDVSAYF YANITGSKHV DLSSRRLIHG  300
KPYVSANESS IAQAADVNFV ANEKVRITKF VGAASTDAFP DPQATAKRAV SEALDAGYQR  360
SLRSHVQEWA SIMHEDSVDR YVNPTTGKLP DDDNIINSAI IAVANTYYLL QNTVGKNAIR  420
AAQDAPLVVN SFSVGGLVSD SYAGLVFWDA DVWMQPGLVA SHPEAAQAVT NYRTKLYPQA  480
KKNIETTYTG SKNATYIDPS AAIYPWTSGR FGNCTGTGAC WDYQYHLNGD IGLSLIYQWV  540
VSGDTNTFRE KHFPIYDSVA ALYGSIVERN GSYWTLTNMT DPDEYANHID AGGFTMPMIS  600
ETLEYANQFR QQFGLEPNET WTEISENVLV LRENGVTLEY TTMNGTAAVK QADIVLVTYP  660
LVYDNYTALT ALTDLDYYAN RQSADGPAMT WAIFSIAAGA VSPSGCSAYT YHQYSYAPYA  720
RAPFFQLSEQ MLDNASINGG THPAYPFLTG HGGANQVVLF GYLGLRLLPD DAIHIEPNLP  780
PQIPYVKYRT FYWRGWPISA QSNYTHTVLQ RSQSAPLDTA DRRFANTSIP VFVGLADNAT  840
LHHLPPHGPL TVRNREIGTI NTIEDNLIQC SPVSSTDAFE QGGFPISVVD GATSTRWQPS  900
SSNASAVTVN LGSTTGRSVQ TVASGFHFDW AAAPPVNASV IFHDTPLSDP VAALSSPGPH  960
VRIVANLTNI EQSGPYDPEA TDLNEIKIPV GNTTRIELAQ EVPVGRYATL VISGNQALAQ 1020
ADGEDHVGAT VAEWAILGPK SGSPRRRIQP VPLL                             1054

SEQ ID NO: 3                   moltype = AA  length = 515
FEATURE                        Location/Qualifiers
source                         1..515
                               mol_type = protein
                               organism = Saccharomycopsis fibuligera
SEQUENCE: 3
MIRLTVFLTA VFAAVASCVP VELDKRNTGH FQAYSGYTVA RSNFTQWIHE QPAVSWYYLL   60
QNIDYPEGQF KSAKPGVVVA SPSTSEPDYF YQWTRDTAIT FLSLIAEVED HSFSNTTLAK  120
VVEYYISNTY TLQRVSNPSG NFDSPNHDGL GEPKFNVDDT AYTASWGRPQ NDGPALRAYA  180
ISRYLNAVAK HNNGKLLLAG QNGIPYSSAS DIYWKIIKPD LQHVSTHWST SGFDLWEENQ  240
GTHFFTALVQ LKALSYGIPL SKTYNDPGFT SWLEKQKDAL NSYINSSGFV NSGKKHIVES  300
PQLSSRGGLD SATYIAALIT HDIGDDDYTP FNVDNSYVL NSLYYLLVDN KNRYKINGNY  360
KAGAAVGRYP EDVYNGVGTS EGNPWQLATA YAGQTFYTLA YNSLKNKKNL VIEKLNYDLY  420
NSFIADLSKI DSSYASKDSL TLTYGSDNYK NVIKSLLQFG DSFLKVLLDH IDDNGQLTEE  480
INRYTGFQAG AVSLTWSSGS LLSANRARNK LIELL                             515

SEQ ID NO: 4                   moltype = AA  length = 757
FEATURE                        Location/Qualifiers
source                         1..757
                               mol_type = protein
                               organism = Bacillus amyloliquefaciens
SEQUENCE: 4
MINQRLFEID EWKIKTNTFQ KEYIRLQESL TSLANGYMGI RGNFEEGYSG GSHQGTYIAG   60
VWFPDKTRVG WWKNGYPDYF GKVINAMNFI GIDVYYDGEK VDLYQNRLES FELELHMKEG  120
ILRRSAVVRI QDKTVRIKSE RFLSLAAKEL CAIHYEAECL TGDAVITLVP YLDGNVVNED  180
SNYQERFWQE KETGADYRRG HITAKTLDNP FGTPRFTVSA LMENLTEGYV SQSFQTSGMY  240
AENRFSYQNK ASLKKFIVVT TSRDVQEAEL TSKGEELLAA ILKQGYEEAR QQHIAKWKER  300
```

```
WAKADIEIKG DEELQQGIRY NIFQLFSTYY GADARLNIGP KGFTGEKYGG AAYWDTEAYA    360
VPMYLATAEP EVTKNLLLYR YHHLEAAKRN AAKLGMKGAL YPMVTFTGDE CHNEWEITFE    420
EIHRNGAICY AICNYVQYTG DRAYMEEYGI DVLVEISRFW AGRVHFSKRK NKYMIHGVTG    480
PNEYENNVNN NWYTNVIAAW TLDYTLQSLE RISAEKRRLL DVQEEELKVU REIIRHMYYP    540
YSEELQIFVQ HDTFLDKDLQ SVDELDPAER PLYQNWSWDK ILRSGFIKQA DVLQGIYLFP    600
DRFSIDEKRR NYEFYEPMTV HESSLSPSIH AVLAAELRME KKALELYKRT ARLDLDNYNR    660
DTEEGLHITS MTGSWLAIVQ GFAGMRTLKG TLSFTPFLPN EWDGYSFHIN YRNRLIKVTV    720
EERRAIFELV KGEPVSITVY GEPMVLNERC ERRMPDE                             757

SEQ ID NO: 5            moltype = AA  length = 1100
FEATURE                 Location/Qualifiers
source                  1..1100
                        mol_type = protein
                        organism = Debaryomyces hansenii
SEQUENCE: 5
MEYDSIGERF KHRTISKIDY CNIFIHKFCK RQIVIKTMVV LNFILIFVLY LYYHGITYAL    60
PPFTIKDIDID DSFNDSTVSF ETIENNKKQL ESLINSRENK EIFLQLQNSG SAYYDPTSNT   120
VGTAEFPTYN QYQRQAYVSN GYIGSRIPNL GQGFTFDQLS DSPDAVEDDL SNGWPLFNER   180
FSGSFIGGFY DIQKNTTETN FPELIEKGYE SILSAVPQWT TLTLSTVKNG KTLSLDPSLS   240
RDSQGDISNY AQNLSLSNGI VTTEFTWLES IQVHFEVVAH RSNINLGIVN LRIVNLDNST   300
VDLKVEDKLD FASTQRCQLS EVGSDEEGIF IHFQPNEIDY VNGAIYSTLQ YDEMSSNAIS   360
RGSTNDTSTQ KLDISVEPSK SFKISKLVGI VSSDLDPEKY KSHNTVNDFA KEVATKQKDS   420
VSKLIKSHKV GWARTFESSN SITFSGDPLL TLASRASIYH LNANTRPGAQ GVTAALPVGG   480
LSSDSYGGMV FWDTDLWMLN GLLPFNPDHA KSIVNYRIHT HEQAIKNVPN NESGAVYSWT   540
SGRFGNCTST GPCLDYEYHI NVAVAMAAWE VYLSGAADDD YLDSVAYPLI NDAATFLADY   600
VKYNESLAQY VSHNMTDPDE YANHVDNAAY TNAGISLLMK WAITISNHLG KPVPSKYTDI   660
AGSMHIPTSD NHDNITLEYT GMNSSVGIKQ ADVIMMTYPL GNELISDDQA YTNMEFYSMK   720
QVSYGPAMTF PIFSIVASNL SPSGCASQSY LHKAVQPFLR GPFAQFSEQN NDNFLTNGGT   780
HPAFPFMTAH GGFLQAILQG LTGLRFDFDL DDRNKLSRML TLDPISLPCL GNGVQFDSIK   840
YMNQSISLAI NETSFIIKHN GPIAGGDSDS IRISLAKRNP KSGVYTLDKG EELVFPLFVP   900
TAGSQLSVSE CASAKFINIT ESAYGDATVL VNDGDNTTHW QLKYNDTTAK ILVDLKQSRN   960
LTSGAINWGD RPPKSWSLLA FGSEEQSKIN DLNDVIDFLS KVNFGNDLYK KYQFIDAGTI  1020
YDQDDVFTTI VSEEVDISAP FDPKDYAEVK IPLRHNTTSF NIEQGLGARF LLIEVTDIHD  1080
TEPIDDETGG AKLYEVEFFE                                              1100

SEQ ID NO: 6            moltype = AA  length = 1072
FEATURE                 Location/Qualifiers
source                  1..1072
                        mol_type = protein
                        organism = Aspergillus niger
SEQUENCE: 6
MQVKFLATLL PLLLHLPAAV DGLPGKNARI SASLKRHAGR DVPQTALNST NVYQTKFSGV    60
TWDEDHWLLT TTTPDQGHYQ SRGSVANGYL GINVANIGPF FELDEPVNGD VINGWPLYSR   120
RQSFATISGF WDRQAHTNGS NFPWLSQYGD DSVISGVPHW SGLILDLGDD TYLDATVDNR   180
TISNFKSTYD FKSGVLSWSY TWTPQGNKGS YAITYRLFAH KLYVNRAVVD MEITPLTNGN   240
ATVVNVLDGY AAVRTDFVAS GQEEGAIFSA VRPWGVNNVT AYVVYATLDGS DSVDLSSRRI   300
VTDKPYVSTN SSSVAQADV MFTANETVRI TKFVGGATTD YVPLATQETAK AACLAGLADG    360
YVKSLQSHVG EWATIMHDHS VDRFTDPATG KLPEDSHIVD SAIIAVTNTY YLLQNTAGTN   420
AIVAAGGIPV NVDSCAPGGL TSDSYGGQIF WDADLWMQPG LVASHPESAQ RFTNYRIALH   480
YQAQANIETA FTGSKNQTSF SSSAAIYPWT SGRFGNCTAT GPCWDYQYHL NGDIGLAMIN   540
QWVASGDTAW FKNYLFPIYD AAATLYSELV ERNGSSWTLT NMTDPDEYAN SINAGGYTMP   600
LIAETLQNAN KLRKQFGLEP NETWDEIAED VLILRENGVT LEYTSMNGSA VVKQADIVLN   660
TFPPLTYESDN YTATNSLTDL DYYANKQSAD GPAMTYAIFA IVASDVSPSG CSAFTYHQYS   720
YAPYARGPWY QLSEQMIDDA SINGGTHPAF PFLTGHGGAN QVALYGYLGL RLHPDDTIYI   780
DPNLPPQIPH ITYRTFYWHG WPISAWSNYT HTTIQRDSSL APLASADLLF SNVSIKVQVG   840
QSTASADEAT IYYLPLSGAL TVPNRMIGSV NTTPGNQVQC HPVYSPDAYE PGQFPISAVD   900
GATSTKWQPS TSDLTSLTVT LSTTAEAGAE EVSGFYFDWS QAPPENLTVI FHDSPIGNPS   960
TVFAAAGSNS TGYRVITSMS NIVQSKPYNA ISAEELNVVS IPTANTTTIT LDAPVQKARY  1020
ATLLIAGNQA NETAGATVAE WVILGQNSTS SSSAQAKRKM SARSKATLAQ LS           1072

SEQ ID NO: 7            moltype = AA  length = 1079
FEATURE                 Location/Qualifiers
source                  1..1079
                        mol_type = protein
                        organism = Trichoderma reesei
SEQUENCE: 7
MRSTVTSAAA LLSLLQLVSP VHGTTLVDRV TKCLSRHDGS DAESHFSKNV YKTDFAGVTW    60
DEDNWLLSTT QLKQGAFEAR GSVANGYLGI NVASVGPFFE VDTEEDGDVI SGWPLFSRRQ   120
SFATVAGFWD AQPQMNGTNF PWLSQYGSDT AISGIPHWSG LVLDLGGGTY LDATVSNKTI   180
SHFRSTYDYK AGVLSWSYKW TPKGNKGSFD ISYRLFANKL HVNQAVVDMQ VTASKNVQAS   240
IVNVLDGFAA VRTDFVESGE DGSAIFAAVR PNGVANVTAY VYADITGSGG VNLSSRKIVH   300
NKPYVHANAS SIAQAVPVKF AAGRTVRVTK FVGAASSDAF KNPKQVAKKA AAAGLSNGYT   360
KSLKAHVEEW ATVMPESSVD SFADPKTGKL PADSHIVDSA IIAVTNTYYL LQNTVGKNGI   420
KAVDGAPVNV DSISVGGLTS DSYAGQIFWD ADLWMQPGLV AAHPEAAERI TNYRLARYGQ   480
AKENVKTAYA GSQNETFFSA SAAVFPWTSG RYGNCTATGP CWDYEYHLNG DIGISLVNQW   540
VVNGDTKDFE KNLFPVYDSV AQLYGNLLRP NKTSWTLTNM TDPDEYANHV DAGGYTMPLI   600
AETLQKANFS RQQFGIEQNK TWNDMASNVL VLRENGVTLE FTAMNGTAVV KQADVIMLTY   660
PLSYGTNYSA QDALNDLDYY ANKQSPDGPA MTYAFFSIVA NEISPSGCSA YTYAQNAFKP   720
YVRAPFYQIS EQLIDDASVN GGTHPAYPPFL TGHGGAHQVV LFGYLGLRLV PDDVIHIEPN   780
```

```
LPPQIPYLRY RTFYWRGWPI SAWSNYTHTT LSRAAGVAAL EGADQRFARK PITIHAGPEQ    840
DPTAYRLPVK GSVVIPNKQI GSQQTYAGNL VQCHAASSPN DYVPGQFPIA AVDGATSTKW    900
QPASADKVSS ITVSLDKEDV GSLVSGFHFD WAQAPPVNAT VIFHDEALAD PATALASAHK    960
HNSKYTTVTS LTNIELSDPY VSTKDLNAIA IPIGNTTNVT LSHPVAASRY ASLLIVGNQG   1020
LDPVDVKAKN GTGATVAEWA IFGHGKEHSG KPSSHSKRRL NVRTAATLSN PRSFMRRRL    1079

SEQ ID NO: 8            moltype = AA   length = 1147
FEATURE                 Location/Qualifiers
source                  1..1147
                        mol_type = protein
                        organism = Kluyveromyces lactis
SEQUENCE: 8
MLIVPFILFS VAILAPIYFY LTKPLPLQHT HFGSFVCAED TLFCPESQRK ASEKMYSLLK     60
DHENTFYDEE QQILGNLLLS ENTFSRQPYV ANGYIGSRIP NLGFGYALDT INVWVNDSSI    120
PGALDNGWPL RNQRFAGAFI SDFYCLQEKL NSTNFPELDD DGYSTVISTI PQWTDLSILK    180
HTTTGQIEYI NPTDVKLDKI TNYMQNLSLQ DGIVTTTFVY DKQLLVTTKV VAHRKIYPLG    240
VVTLELSLFD NNSDTSADNE NEYVELEICD SLNFSTSHRT VLNDYGYDQN NEGIFMVVEP    300
ENVPYSNASL FSYFDIPSRD TLTLSKYSDS ISQCTTQILK ANSTFVAHKY IGIISSEYDN    360
KQPDDNSNGT SNEALKMSNL ERATSIVLDN KGNYDSLIQS HKNAWKRIYK DASIEIPSDG    420
LLEMTAKSSI YHLLANTRSH NVSEDRGLPI GVSGLSSDSY GGMVFWDSDL WILPALLPFF    480
PNAARQINNY RNASLHQAKL NAEKYGYDGA LYPWTSGRYA NCTSTGPCVD YEYHINVDIA    540
LSSFAIYMNG DEDDERSEEY LRYTTWPFVE NAAKMFAQYV KWNDTMQQYT THNLTDPDEY    600
ANFVDNAAFT NAGIQSVMVW AHDIARHLGI DPDPQWLEIA DNIHIPISET NITLEYSGMN    660
SSVEIKQADV VLMIYPLSYI TDQSILNNAI KNLYYYSERQ SASGPAMTYP VFVAGAASLL    720
NYGSSSQSYL YKSVVPYLRS PFAQFSEQSD DNFLTNGLTQ PAFPFLTANG GFLQSILFGL    780
TGLRYSYEVD EDTGKIHRLL KFNPIQLPLL PGGIRINNFK YMGQVLDVLI TDTEGIIIHK    840
NGTKEIRIKV PDRTLIPDVD VKYSEETDPI KQILHGRRSV PTGKNYFTIQ PGDVFKTPLY    900
IPKKNLEGNL VEAKQITNLT AGVPGDVAVS VIDGNNFTHW QPAYKNLPAR LLIDMGNNFT    960
QEIKSGKIIW GSRPAKTFSL SILPQTEEVF KNLTHILSNV NQYCNKTGDE CVRDLERTEK   1020
GFDAAIEDVF DWYGIDPDSI ISTHPELKDM KTKFVKILDH YKVTPSEPYP WRVYNESQIV   1080
LLPGNETDFD IDYSKVAEMN PENVDIDFRG NQTDWRKGRF IVLTVHDTYD DDDDEKGATI   1140
KEFALFP                                                            1147

SEQ ID NO: 9            moltype = AA   length = 735
FEATURE                 Location/Qualifiers
source                  1..735
                        mol_type = protein
                        organism = Schizosaccharomyces pombe
SEQUENCE: 9
MPSKFSSKYV DTEAISNDDD NPFATAKSYY SKDTDLSTRV SAGRPRTLST SMEASAAPTI     60
PELKNLRRRG SLDEHKQPRK FLVDVDKTLN ALLESEDTDR NMQITIEDTG PKVVSLGSAS    120
SGGYRLYELR GTYQLSNLLQ ELTLAKDYGR RYILLDERRL NENPVNRLSR LIKGTFWDAL    180
TRRIDASVLD VICRDTKDRS GSHVNRIYVP KAEQEMYEYY VRAAKERPYL NLQVEYLPEE    240
ITPEWVRDVN DKPGLLALAM EKYQDDEGNT HLRGVPFVVP GGRFNELYGW DSYFESLGLL    300
VDDRVDLAKG MVENFIFEIT YYGKILNANR TYYLLRSQPP FLTDMALRVY ERIKNEEGSL    360
DFLHRAFSAT IKEYHTVWTA TPRLDPKTGL SRYRPGGLGI PPETEASHFE HLLRPYMEKY    420
HMTLEEFTHA YNYQQIHEPA LDEYFVHDRA VRESGHDTYY RLEKVCADLA TVDLNSLLYK    480
YETDISHVIL EYFDDKFVLP NGTIETSAIW DRRARARRAA MEKYLWSEAD SMWYDYNTKL    540
ETKSTYESAT AFWALWAGVA TPRQAAKFVD VSLPKFEVAG GIVAGTKRSL GKVGLDNPSR    600
QWDYPNGWSP QQILAWYGLI RYGYEEETRR LVYRWLYTIT KSFVDFNGIV VEKYDLTRPV    660
DPHRVEAEYG NQGVNIKGVA REGFGWVNAS YEVGLTFCNS HMRRALGACT TPDVFFAGIK    720
EESLPAFENL SIHKN                                                    735

SEQ ID NO: 10           moltype = AA   length = 744
FEATURE                 Location/Qualifiers
source                  1..744
                        mol_type = protein
                        organism = Neurospora crassa
SEQUENCE: 10
MTSQPSSGKG RGRNLSIDEY NVYDDAKTYY TTEDRHHNHR AGARTRTYSQ NSLFKQFERL     60
GLQKEPYRRG SHDESTIPQS RRFLIQVEPT LQSLQSQEDT DGNMQITIED NGPKVLSLRT    120
AASNGYNRFD IRGTYMLSNL LQELYLAKEY GRKQIILDEA RLNENPVNRL SRLIKDHFWE    180
GLTRRIDASS IEIAARDPKD WTDDPRPRIY IPRGAPEQHE YYTKVALDRP ELRLDVQYLP    240
EKITPEIVRD MNAKPGLLAV DMEEVVDPKT GEKTLRGRPF VVPGGRFNEL YGWDSYMESL    300
GLLVNDRVDL AKSMVQNFCF CIKHYGKILN ATRSYYLCRS QPPFLTDMTL RVYDKIKHEP    360
GALEFLRQSL LAAIKEYYSV WTAEPRLDPV TGLSRYRPEG LGVPPETEAG HFIHILEPYA    420
KKHNMSFDEF VYAYNHGEIK EPTLDDYFMH DRAVRESGHD TTYRFEGICA DLATIDLNSL    480
LFKYETDIAR TIRNVPHDKF EVPDDWLATN NPAASKLETS AMWDRRAKRR KLAIDKYLWN    540
EEAGMYFDYN TATRKQCNYE SATTFWALWA GVSNPKQAAA MVTKALPKLE AFGGLLSGTK    600
ESRGEIGLER PNRQWDYPYG WAPQQILAWT GLYRYGFNEE AERLAYKWLF MITKAFVDFN    660
GVVVEKYDVT RPIDPHRVDA EYGNQGLDFK GVAKEGFGWV NASYVYGLQI VNAHMRRALG    720
TLTPYETFMK AVEENRNKAL SELV                                          744

SEQ ID NO: 11           moltype = AA   length = 907
FEATURE                 Location/Qualifiers
source                  1..907
                        mol_type = protein
                        organism = Candida albicans
SEQUENCE: 11
```

```
MFTKNHRRMS STSSDDDPFD VAEKYYGEER KKKLNRVRTF SAFESTKYGA GPISPLRPTY   60
EPPPVIKETS EPLSSSSSTS SPPTLTPQTS QVQFNLGVGK TKNGSAIHSD SEEEEEDEDP  120
VSNTKKGEAD EKDPFDTTDS KLENENSTPS SITGKEIIPH PTGFRGSSEE SAIRRKPSII  180
PIYHDNISQE SVIRNANTPT TYNREKFHLR RGSLDESTFI RPKKYYINDV QGTLRELLAN  240
EDTDNNCQIT IEDTGPKVLR LGTANSLGIN QSSIRGTYRL SNLLQELTIA SRFGRHQIVL  300
DEARLSENPV DRMKRLISTS FWNNLTRIIT KENIVDMAKD TKIKESWIDD QGKLHENQES  360
HRIYVPYNRK DQYEFFQLIK KQRSDIQLDV QYLPQKIDAD YIKSINKKPG LLSIATRPDP  420
QAPDSGSLIS WPYVVPGGRF NELYGWDSYM ETLGLLTDVK IDPSGNPRNL RHLELARGMA  480
ENFIYEIHHY GKILNANRSY YLGRSQPPFL TDMALRIFNK TIEVTPELMD EAIDFLKRAT  540
LAAIKEYETI WCAHPRLDDK TGLSCYHPEG KGIPPETEPT HFNALLKPYL AKYNDIDQLD  600
FIEKYNSGEI KEPELDEYFL HDRAVRESGH DTSYRLEGKC AYLATVDLNS LLYKYENDIA  660
FILQSFFNDN LQDPYDDNNS NKIHSSKIWL ERSHQRKLNV DKYLWNEQDG IYYDYNVKLQ  720
QQTNYESATT FWPLYAKLAS SNQAAKLIDQ SLHKFEEHGG LVAGTLKSRG EVGLTRPSRQ  780
WDYPFGWAPQ QILAWIGLVN YGYDGIARRL AYRWLFMMTK SFVDYNGVIV EKYNVTKGAV  840
PHRVDAEYGN QGLDFKGVAT EGFGWVNASY VFGLTFLNLY AQRALGSLTP PEIFLRNMHP  900
EQRKQYK                                                          907

SEQ ID NO: 12          moltype = AA  length = 1100
FEATURE                Location/Qualifiers
source                 1..1100
                       mol_type = protein
                       organism = Debaryomyces hansenii
SEQUENCE: 12
MEYDSIGERF KHRTISKIDY CNIFIHKFCK RQIVIKTMVV LNFILIFVLY SYYHGITYAL   60
PPFTIKDIDID DSFNDSTVSF ETIENNKKQL ESLINSRENK EIFLQLQNSG SAYYDPTSNT  120
VGTAEPPTYN QYQRQAYVSN GYIGSRIPNL GQGFTFDQLS DSPDAVEDDL SNGWPLFNER  180
FSGSFIGGFY DIQKNTTETN FPELIEKGYE SILSAVPQWT TLTLSTVKNG KTLSLDPSLS  240
RDSQGDISNY AQNLSLSNGI VTTEFTWLES IQVHFEVVAH RSNINLGIVN LRIVNLDNST  300
VDLKVEDKLD FASTQRCQLS EVGSDEEGIF IHFQPNEIDY VNGAIYSTLQ YDEMSSNAIS  360
RGSTNDTSTQ KLDISVEPSK SFKISKLVGI VSSDLDPEKS KSHNTVNDFA KEVATKQKDS  420
VSKLIKSHKV GWARTFESSN SITFSGDPLL TLASRASIYH LNANTRPGAQ GVTAALPVGG  480
LSSDSYGGMV FWDTDLWMLN GLLPFNPDHA KSIVNYRIHT HEQAIKNVPN NESGAVYSWT  540
SGRFGNCTST GPCLDYEYHI NVAVAMAAWE VYLSGAADDD YLDSVAYPLI NDAATFLADY  600
VKYNESLAQY VSHNMTDPDE YANHVDNAAY TNAGISLLMK WAITISNHLG KPVPSKYTDI  660
AGSMHIPTSD NHDNITLEYT GMNSSVGIKQ ADVIMMTYPL GNELISDDQA YTNMEFYSMK  720
QVSYGPAMTF PIFSIVASNL SPSGCASQSY LHKAVQPFLR GPFAQFSEQN NDNFLTNGGT  780
HPAFPFMTAH GGFLQAILQG LTGLRFDFDL DDRNKLSRML TLDPISLPCL GNGVQFDSIK  840
YMNQSISLAI NETSFIIKHN GPIAGGDSDS IRISLAKRNP KSGVYTLDKG EELVFPLFVP  900
TAGSQLSVSE CASAKFINIT ESAYGDATVS VNDGDNTTHW QSKYNDTTAK ILVDLKQSRN  960
LTSGAINWGD RPPKSWSLSA FGSEEQSKIN DLNDVIDFLS KVNFGNDLYK KYQFIDAGTI 1020
YDQDDVFTTI VSEEVDISAP FDPKDYAEVK IPSRHNTTSF NIEQGLGARF LLIEVTDIHD 1080
TEPIDDETGG AKLYEVEFFE                                            1100

SEQ ID NO: 13          moltype = AA  length = 1212
FEATURE                Location/Qualifiers
source                 1..1212
                       mol_type = protein
                       organism = Candida glabrata
SEQUENCE: 13
MGFKDKILFW KDEVQYRTLA VADQVANRFL HSFENVYQGD ESVEDADSRP VGLTNETLSH   60
SSDFFVLPEE RISTRVKIRR QNILNTTLIL GMLIALVIWT AILSTNSYFS SSLASASPLF  120
NKEGRVVRPM RESNLGLHAD PQTRKSSKTL YDLLSDFDNA FYDDENMILG SLAFGENTYS  180
RQPYVANGYI GSRIPNIGFG YALDTLNLYA DAPGALNNGW PLRNRRFAGS FVSDFYSLQA  240
KLNSTNFPEL DEKGYTTVIS SIPEWTDLQF TVDLNGTKWF NPQSVLIDDV INYNQNLSMK  300
DGIVSTNMDW LNGMINIKSE VWAHRKIHSL GITRLEISLN LDALPDEFTE LPVTVYDIID  360
LNTSHRTTLY EKGQDEDNKA IYMIVNPDNV PYSNAVVYST CTIKGTENNF SPYNFTSDDR  420
IARNYMTNLT EENPKVVIYK YTSVVSSEYN NDEPNPNVNL KFASNIANTA KGNYKSLLSN  480
HKRAWYDLYN DAFIEIPSDS LLEMTARSSL FHLLANTRQY NVSTTRGLPV GVGGLSSDSY  540
GGMVFWDADV WMAPALLPFF PNIAMNMNNY RNATHQQAIE NAKQYNYPGA VYPWTSGRYA  600
NCTSTGPCID YEYHINVDIA LASFSIYMNG AEGADEDYLR FTTWPMVKDA AVFFKAYVKY  660
NETLGEYETY NLTDPDEFAN HVNNGAFTNA GIKTLLKWAT DIGTHLGEEV DPKWMEIADN  720
IHIPRSDSNI TLEYSGMNSS VEIKQADVTL MVYPLGYIND ESILNNAIKD LYYYSERQSA  780
SGPAMTYPVF VAAAASLLNH GSSSQSYLYK SVLPYLRSPF AQFSEQSDDN FLTNGLTQPA  840
FPPFLTANGGF LQSILFGLTG LRYSYEVTPR TKKISRLLKF DPVKLPLLPG GIAIRNFKYM  900
GQVLDIIIDD NNGTIAHKGG DKPIRIKVPN RDILHDRNIT SALYSKRDDD LSATDDYYGT  960
YFTLYPNEEL VIPLYDTKLN IDGNIAESKQ ITNLTAGVPG DVGFSALDGN NYTHWQPFDK 1020
SDNAKLLIDL GFNSTHVIKK GIILWGQRPA KNISLSVLPH SERIEQLFAN ITDLLETSSI 1080
TKGGLPLNQM LGQTQSNVTA EIDDDILALL NWKGDDLDQL IPYLPDMHLL QEKFIPILKD 1140
YPIKPNQRYY EEIIDDDIIK LLPSNTTEFT IDYNSIPGGE KRARYVVLTV HGTYDDDDDL 1200
KGATIREIVL QE                                                    1212

SEQ ID NO: 14          moltype = AA  length = 754
FEATURE                Location/Qualifiers
source                 1..754
                       mol_type = protein
                       organism = Kluyveromyces lactis
SEQUENCE: 14
MDGKVNNNPP RSRHRRTSSL EEVVDPFSTP DVYYGPKSDP SKLLSKNRFT RTRTFSVAEP   60
GGGKGHSSSY TSPYFDTTVP LRRRGSEDDS YSASQGQRRF YIEDVDKTLK ELLASEDTDG  120
```

```
NYQITIEDTG  PKVIRVGTVN  SNGYKHVHIR  GTYMLSNLLQ  ELTLAKLFNR  KQVILDEARL   180
NENPVNRMTR  LISGQFWKSL  TRRIDSNNIA  KIAYDTKIDT  PKAKNPRIYV  PYNCQDEYQQ   240
LVQWSEMDPS  LQLEVNYLPK  DITPEFVKSL  NDKPGLLCLA  MESHMDPVTG  EETWVGFPYA   300
VPGGRFNELY  GWDSYFMALG  LLESNKLDVA  RGMVEHFIFE  IDHYGKILNA  NRSYYLCRSQ   360
PPFLTDMALQ  VCRKMGGDKN  PVAVDLLRRA  FKAAIKEYLT  VWTASPRLDE  KTGLSCYHPD   420
GIGIPPETEP  GHFDSILRKY  AEKYNVSIPE  FRDLYNSQKV  HEPDLDVFFL  HDRGVRESGH   480
DTTYRFENVC  AYLATIDLNS  LLYKYEVDIA  YVIKKYFGDN  FEGLPEGHRT  SNDWEKLAEV   540
RKERIDKYLW  DEETGFYYDY  NVKTEKRTSY  ESVTTFWALW  AGMSSQEQAQ  RMVENALPKL   600
EEFGGLVACT  ARSRGELSLD  RPTRQWDYPF  GWAPHQILVW  DGLVRYGYEN  HTRRLAYRWL   660
FLMTKAFVDY  NGIVVEKYDV  TRGTDPHRVD  AEYGNQGADF  KGVATEGFGW  VNSSYLLGMK   720
YMNNFARRAL  GTCVTPKVFF  GRLPPKEKKK  YGLE                                754

SEQ ID NO: 15           moltype = AA  length = 1066
FEATURE                 Location/Qualifiers
source                  1..1066
                        mol_type = protein
                        organism = Rasamsonia emersonii
SEQUENCE: 15
MQSKLLSLLL  LSLPASCLPL  EERVAQVVRA  YSSPHGLQVR  DGKPANASQT  YETRFPGVTW    60
DQHNWRLTST  VLDQGHYQSR  GSIANGYVGI  NVASAGPFFE  LDTPVGGDVI  NGWPLFSRRQ   120
TFATIAGFYD  EQPRTNGTNF  PWLYQYGGES  VISGVPHWSG  LVLDLGDGTY  LDATVDNTTI   180
SDYSTVVDYK  AGILSWSYTW  TPTGNKGSFK  INYSLFAHKL  YVNQAVVRLD  ITPSTNTNAT   240
VVNVIDGYSA  VPTDFVGSGK  DGSIYSAVRP  WGINNVTAYI  YTVLDGSNGV  DLSSAAIVSN   300
KPYIHTNDSS  IAQSVNVGFR  SGKTVSITKL  VGAASSDAFP  NPQQTAKEAA  LTAKKKGYEA   360
LLRSHVKEWA  AVMPDDSVDD  FTFPENGTLP  QDPPIIESAI  TAVVNPYYLL  QNTVSENALK   420
EISNAPANEW  SISVGGLTSD  SYPGFHFLGR  QICGMHLGLV  VFSPKQPRGI  PQITGKPSTS   480
KPAKTLRLAF  TSSKNKTWFS  DSAAVYPWTS  GRYGNCTGTG  PCWDYEYHLN  GDIGLSLINQ   540
WVTSGDTKTF  QESYFPIYDS  IATLYADLLR  LNGSHWTLTN  MTDPDEYANP  VNAGGYTMLL   600
IAQTLFYANS  FRQQFGIAKN  TTWTDMASNI  LLLRENDVTL  EYTTMNNSVA  VKQADVVLVT   660
YPLDYSTNYS  SSDALNDLDY  YALKQSPDGP  GMTYAIFSIV  ANEVSPSGCS  VYTYAQYSYD   720
PYVRAPFFQF  SEQLIDDYTL  NGGTHPAYPF  LTGHGGANQV  VIFGYLGLRL  LPDDAIHIDP   780
NLPPQVPHVK  YRTFYWRGWP  IQASSNYTHF  TISRAAHVQP  LDTADQRFAK  TAIPVQVGSG   840
KNVTVYQLPL  KGQLTVPNHQ  VGSTLTVPGN  LAQCQPVQSQ  NSYEPGQYPM  AAVDGAASTK   900
WQPSFAANTS  SLTVSLPASE  SGAMVSGFYF  DWAQAPPVKA  TVVFHNDTSD  DPLATSSNGQ   960
SLSRILATLP  FLVLTTPEAT  RADTIMFRGG  NTTNVTLAQP  VPGATVRHFC  ISPAIKRSAS  1020
QVRPRTARAR  RLQSGRFWRT  TLRSNSRSER  FRWSVSSPAL  AGLHAR                  1066

SEQ ID NO: 16           moltype = AA  length = 738
FEATURE                 Location/Qualifiers
source                  1..738
                        mol_type = protein
                        organism = Ashbya gossypii
SEQUENCE: 16
MLQGMPKRSG  SISELHDPFS  SPDVYYGPAT  DPRRQKQPNK  YSRTRTMSII  ENVSTFKSAG    60
KQYNIRRRGS  EDDSMLASSG  HRKFYIKDVD  KTLEELLESE  DTDGNYQITI  EDRGPKTLRV   120
GTANSNGFRH  VQIRGTYMLS  NLLQELTIAK  NFGRKQVILD  EARLNEDPVN  RLTRLITHQF   180
WDSLTRRIDY  NSIAAIAADT  KVDTPGAKVP  RIYVPHGCPE  QYEYFIECSQ  LNPSLNLEVK   240
YLPDVITPEH  VQSLNESPGL  LALAMESHRD  PITGESTLVG  FPYVVPGGRF  NELYGWDSYL   300
MALGLLDCNK  VDIARGMVEH  FIFEIEHYGK  ILNANRSYYL  CRSQPPFLTD  MALKVFEKFG   360
GDQNPTAVDF  LKRAFIAAIK  EYKSVWMAEP  RYDKTTGLSC  YHPDGIGFPP  ETEPDHFDAI   420
CRKFAEKHNV  TIPEFRCMYD  AGEVHEPELD  EFFLHDRAVR  ESGHDTSYRL  ENVCAYLATI   480
DLNSLLYKYE  KDIAYVVSKY  FDDSITDYAG  ETTTSSHWEA  LADIRKQRIT  KYLWDEETGF   540
FYDYNVHIGK  RTSYDSATTF  WAMWAGLATQ  EQANAMVEKA  LPRLEMLGGL  VACTEESRGE   600
ITMNRPSRQW  DYPYGWAPHQ  MLAWTGLDNY  GFTGVARRLA  YRWLFLMTKA  FVDYNGIVVE   660
KYDVTRGTDP  HRVDAEYGNQ  GADFKGVATE  GFGWVNSSYI  LGLKFMNTYA  KRALANCTVP   720
DIFFKHMKPE  EKARYALI                                                    738

SEQ ID NO: 17           moltype = AA  length = 698
FEATURE                 Location/Qualifiers
source                  1..698
                        mol_type = protein
                        organism = Magnaporthe oryzae
SEQUENCE: 17
MSPLWKTAAA  IAVAASGSLV  NAVYINGSII  TPCDSLIYCR  GELLKEVELA  HPFADSKTFV    60
DMPTIKPVDE  VIEAFNKLQK  PLSNNTELQD  FLRENFAQAG  GELEEVPNSE  LETDPVFLDK   120
LDDTVIREFV  EKVIDIWPSL  TRRYKGPSNC  EACADSFIPV  NRTFVVAGGR  FREPYYWDSY   180
WILEGLLRTG  GAFTNISKNT  VENFLDLVET  IGFVPNGARI  YYKNRSQPPL  LSQMVRIYVE   240
HTNDTSILGR  AVPLLIKEHE  FFINNRSIDV  EASNGKTYRL  QRYAVTNTQP  RPESYREDYI   300
TASNRSYYSP  SGIIYPESHQ  LNESEKAVLY  SHLASGAESG  WDYTSRWLST  PSDAVRDNYF   360
PLRSLNTNNI  VPVDLNSILY  ANEVAIAEFL  NRTGNSTGAS  DWMDLAKQRS  EAMYALMWNE   420
TLWSYFDYNM  TSKTQNRFIP  VDEDAVSIET  NNAPAGQQVF  FHVAQYYPFW  TGAAPRSLKN   480
NPLAVLRAYE  RIDAYLDIKR  GAIPATNLKT  GQQWDEPNVW  PPLMHILMEG  LTRVPATFGE   540
DDVAWTEIQD  LALRLGQRYL  DSTFCTWYAT  GGSTSETPQL  QGLNAEDKGI  MFEKYGDNST   600
NVAGSGGEYE  VVEGFGWTNG  VLMWVADTFN  NKLTRPDCGN  ITAANVHSDG  SQARKRGEMW   660
SALEMHPYDA  AWTKEFGARK  VRRDKAEARA  LGNVMGGV                            698

SEQ ID NO: 18           moltype = AA  length = 528
FEATURE                 Location/Qualifiers
source                  1..528
```

```
                            mol_type = protein
                            organism = Thermus thermophiles
SEQUENCE: 18
MWWKEAVIYQ  VYPRSFQDTN  GDGVGDLEGV  RRRLPYLKSL  GVDALWLSPF  YKSPMKDFGY   60
DVADYCDVDP  VFGTLQDFDR  LLEEAHALGL  KVLVDLVPNH  TSSEHPWFLE  SRASRNSPKR  120
DWYIWKDPAP  DGGPPNNWQS  FFGGPAWTLD  EATGQYYLHQ  FLPEQPDLNW  RNPEVREAIY  180
EVMRFWLRRG  VDGFRVDVLW  LLAEDLLFRD  EPGNPDWRPG  MWDRGRHLHI  FTEDQPETYA  240
YVREMRQVLD  EFSEPGRERV  MVGEIYLPYP  QLVRYYQAGC  HLPFNFHLIF  RGLPDWRPEN  300
LARIVEEYES  LLTRWDWPNW  VLGNHDQPRL  ASRLGEAQAR  VAAMLLFTLR  GTPTWYYGDE  360
IGMKNGEIPP  EKVQDPAALR  QKDRLGEHNL  PPGRDPERTP  MQWDDTPFAG  FSTVEPWLPV  420
NPDYKTRNVA  AQEQDPRSML  HLVRRLIALR  KDPDLLYGAY  RTYRAREGVY  AYLRGEGWLV  480
ALNLTEKEKA  LELPRGGRVV  LSTHLDREER  VGERLFLRPD  EGVAVRLD                528

SEQ ID NO: 19           moltype = DNA   length = 36
FEATURE                 Location/Qualifiers
misc_feature            1..36
                        note = Primer Oligonucleotide
source                  1..36
                        mol_type = other DNA
                        organism = synthetic construct
SEQUENCE: 19
gcagaggatt acttggacat taacggttct cctatc                                  36

SEQ ID NO: 20           moltype = DNA   length = 60
FEATURE                 Location/Qualifiers
misc_feature            1..60
                        note = Primer Oligonucleotide
source                  1..60
                        mol_type = other DNA
                        organism = synthetic construct
SEQUENCE: 20
ggacgaggca agctaaacag atctctagac ctaagttcta tgtcttaata agtctgtatg        60

SEQ ID NO: 21           moltype = DNA   length = 60
FEATURE                 Location/Qualifiers
misc_feature            1..60
                        note = Primer Oligonucleotide
source                  1..60
                        mol_type = other DNA
                        organism = synthetic construct
SEQUENCE: 21
tactcacata cagacttatt aagacataga acttaggtct agagatctgt ttagcttgcc        60

SEQ ID NO: 22           moltype = DNA   length = 60
FEATURE                 Location/Qualifiers
misc_feature            1..60
                        note = Primer Oligonucleotide
source                  1..60
                        mol_type = other DNA
                        organism = synthetic construct
SEQUENCE: 22
gaatagacga tcgtctcatt tgcatcgggt tcagagacta catgatagtc caaagaaaag        60

SEQ ID NO: 23           moltype = DNA   length = 60
FEATURE                 Location/Qualifiers
misc_feature            1..60
                        note = Primer Oligonucleotide
source                  1..60
                        mol_type = other DNA
                        organism = synthetic construct
SEQUENCE: 23
ccgtttcttt tctttggact atcatgtagt ctctgaaccc gatgcaaatg agacgatcgt        60

SEQ ID NO: 24           moltype = DNA   length = 36
FEATURE                 Location/Qualifiers
misc_feature            1..36
                        note = Primer Oligonucleotide
source                  1..36
                        mol_type = other DNA
                        organism = synthetic construct
SEQUENCE: 24
gcaagaggct cctccactgg cattttcacg atttgg                                  36

SEQ ID NO: 25           moltype = DNA   length = 35
FEATURE                 Location/Qualifiers
misc_feature            1..35
                        note = Primer Oligonucleotide
source                  1..35
                        mol_type = other DNA
```

```
                           organism = synthetic construct
SEQUENCE: 25
gctgtgcagc agggtattct actacgtgtt agctt                                35

SEQ ID NO: 26              moltype = DNA   length = 60
FEATURE                    Location/Qualifiers
misc_feature               1..60
                           note = Primer Oligonucleotide
source                     1..60
                           mol_type = other DNA
                           organism = synthetic construct
SEQUENCE: 26
ggacgaggca agctaaacag atctctagac ctattcggca cagaaatagt gacaggcagt    60

SEQ ID NO: 27              moltype = DNA   length = 60
FEATURE                    Location/Qualifiers
misc_feature               1..60
                           note = Primer Oligonucleotide
source                     1..60
                           mol_type = other DNA
                           organism = synthetic construct
SEQUENCE: 27
aataacactg cctgtcacta tttctgtgcc gataggtct agagatctgt ttagcttgcc     60

SEQ ID NO: 28              moltype = DNA   length = 60
FEATURE                    Location/Qualifiers
misc_feature               1..60
                           note = Primer Oligonucleotide
source                     1..60
                           mol_type = other DNA
                           organism = synthetic construct
SEQUENCE: 28
tctagtcata accatttcgt taaaaagggt gttgagacta catgatagtc caaagaaaag    60

SEQ ID NO: 29              moltype = DNA   length = 60
FEATURE                    Location/Qualifiers
misc_feature               1..60
                           note = Primer Oligonucleotide
source                     1..60
                           mol_type = other DNA
                           organism = synthetic construct
SEQUENCE: 29
ccgtttcttt tctttggact atcatgtagt ctcaacaccc ttttaacga aatggttatg    60

SEQ ID NO: 30              moltype = DNA   length = 31
FEATURE                    Location/Qualifiers
misc_feature               1..31
                           note = Primer Oligonucleotide
source                     1..31
                           mol_type = other DNA
                           organism = synthetic construct
SEQUENCE: 30
cgtagatcga ccttgcctgg aatcccaggt t                                    31

SEQ ID NO: 31              moltype = DNA   length = 32
FEATURE                    Location/Qualifiers
misc_feature               1..32
                           note = Primer Oligonucleotide
source                     1..32
                           mol_type = other DNA
                           organism = synthetic construct
SEQUENCE: 31
ctcgttggta gggtccacac catagacttc ag                                   32

SEQ ID NO: 32              moltype = DNA   length = 35
FEATURE                    Location/Qualifiers
misc_feature               1..35
                           note = Primer Oligonucleotide
source                     1..35
                           mol_type = other DNA
                           organism = synthetic construct
SEQUENCE: 32
tagctatgaa attttaact ctttaagctg gctct                                35

SEQ ID NO: 33              moltype = DNA   length = 60
FEATURE                    Location/Qualifiers
misc_feature               1..60
                           note = Primer Oligonucleotide
source                     1..60
```

```
                        mol_type = other DNA
                        organism = synthetic construct
SEQUENCE: 33
gatgagagcc agcttaaaga gttaaaaatt tcatagctag ggcgccataa ccaaggtatc    60

SEQ ID NO: 34           moltype = DNA   length = 60
FEATURE                 Location/Qualifiers
misc_feature            1..60
                        note = Primer Oligonucleotide
source                  1..60
                        mol_type = other DNA
                        organism = synthetic construct
SEQUENCE: 34
ccaacaaaga aacccaagta gccaagtttt gagacaacat gtttagttaa ttatagttcg    60

SEQ ID NO: 35           moltype = DNA   length = 54
FEATURE                 Location/Qualifiers
misc_feature            1..54
                        note = Primer Oligonucleotide
source                  1..54
                        mol_type = other DNA
                        organism = synthetic construct
SEQUENCE: 35
gaatatacgg tcaacgaact ataattaact aaacatgttg tctcaaaact tggc          54

SEQ ID NO: 36           moltype = DNA   length = 58
FEATURE                 Location/Qualifiers
misc_feature            1..58
                        note = Primer Oligonucleotide
source                  1..58
                        mol_type = other DNA
                        organism = synthetic construct
SEQUENCE: 36
caaagacttt cataaaaagt ttgggtgcgt aacacgctat caagcgttga attgtctg      58

SEQ ID NO: 37           moltype = DNA   length = 60
FEATURE                 Location/Qualifiers
misc_feature            1..60
                        note = Primer Oligonucleotide
source                  1..60
                        mol_type = other DNA
                        organism = synthetic construct
SEQUENCE: 37
gctttgaacg acagaagata cagacaattc aacgcttgat agcgtgttac gcacccaaac    60

SEQ ID NO: 38           moltype = DNA   length = 60
FEATURE                 Location/Qualifiers
misc_feature            1..60
                        note = Primer Oligonucleotide
source                  1..60
                        mol_type = other DNA
                        organism = synthetic construct
SEQUENCE: 38
tatataaaat taaatacgta aatacagcgt gctgcgtgct atgaggaaga aatccaaatc    60

SEQ ID NO: 39           moltype = DNA   length = 35
FEATURE                 Location/Qualifiers
misc_feature            1..35
                        note = Primer Oligonucleotide
source                  1..35
                        mol_type = other DNA
                        organism = synthetic construct
SEQUENCE: 39
agcacgcagc acgctgtatt tacgtattta atttt                               35

SEQ ID NO: 40           moltype = DNA   length = 35
FEATURE                 Location/Qualifiers
misc_feature            1..35
                        note = Primer Oligonucleotide
source                  1..35
                        mol_type = other DNA
                        organism = synthetic construct
SEQUENCE: 40
gtagtgctgt ctgaacagaa taaatgcgtt cttgg                               35

SEQ ID NO: 41           moltype = DNA   length = 30
FEATURE                 Location/Qualifiers
misc_feature            1..30
                        note = Primer Oligonucleotide
```

```
source                     1..30
                           mol_type = other DNA
                           organism = synthetic construct
SEQUENCE: 41
ctgactcgtt ggtggggtcc acaccataga                                      30

SEQ ID NO: 42              moltype = DNA   length = 60
FEATURE                    Location/Qualifiers
misc_feature               1..60
                           note = Primer Oligonucleotide
source                     1..60
                           mol_type = other DNA
                           organism = synthetic construct
SEQUENCE: 42
gattggcggt ctatagatac cttggttatg gcgccctagc tatgaaattt ttaactcttc      60

SEQ ID NO: 43              moltype = DNA   length = 60
FEATURE                    Location/Qualifiers
misc_feature               1..60
                           note = Primer Oligonucleotide
source                     1..60
                           mol_type = other DNA
                           organism = synthetic construct
SEQUENCE: 43
gagagccagc tttttgaaga gttaaaaatt tcatagctag ggcgccataa ccaaggtatc      60

SEQ ID NO: 44              moltype = DNA   length = 20
FEATURE                    Location/Qualifiers
misc_feature               1..20
                           note = Primer Oligonucleotide
source                     1..20
                           mol_type = other DNA
                           organism = synthetic construct
SEQUENCE: 44
gtttagttaa ttatagttcg                                                 20

SEQ ID NO: 45              moltype = DNA   length = 60
FEATURE                    Location/Qualifiers
misc_feature               1..60
                           note = PrimerOligonucleotide
source                     1..60
                           mol_type = other DNA
                           organism = synthetic construct
SEQUENCE: 45
tttttagaat atacggtcaa cgaactataa ttaactaaac atgagattca agtccgtttt      60

SEQ ID NO: 46              moltype = DNA   length = 60
FEATURE                    Location/Qualifiers
misc_feature               1..60
                           note = PrimerOligonucleotide
source                     1..60
                           mol_type = other DNA
                           organism = synthetic construct
SEQUENCE: 46
aatgaaaaaa aaagtggtag attgggctac gtaaattcga ttacaacaaa ggaactggtt     60

SEQ ID NO: 47              moltype = DNA   length = 21
FEATURE                    Location/Qualifiers
misc_feature               1..21
                           note = Primer Oligonucleotide
source                     1..21
                           mol_type = other DNA
                           organism = synthetic construct
SEQUENCE: 47
tcgaatttac gtagcccaat c                                               21

SEQ ID NO: 48              moltype = DNA   length = 60
FEATURE                    Location/Qualifiers
misc_feature               1..60
                           note = Primer Oligonucleotide
source                     1..60
                           mol_type = other DNA
                           organism = synthetic construct
SEQUENCE: 48
tatataaaat taaatacgta aatcagcgt gctgcgtgct caaatgacgt caaaagaagt       60

SEQ ID NO: 49              moltype = DNA   length = 60
FEATURE                    Location/Qualifiers
misc_feature               1..60
```

```
                        note = Primer Oligonucleotide
source                  1..60
                        mol_type = other DNA
                        organism = synthetic construct
SEQUENCE: 49
cataggctca tataatactt cttttgacgt catttgagca cgcagcacgc tgtatttacg   60

SEQ ID NO: 50           moltype = DNA  length = 32
FEATURE                 Location/Qualifiers
misc_feature            1..32
                        note = Primer Oligonucleotide
source                  1..32
                        mol_type = other DNA
                        organism = synthetic construct
SEQUENCE: 50
gtagtgctgt ctgaacagaa taaatgcgtt ct                                 32

SEQ ID NO: 51           moltype = DNA  length = 33
FEATURE                 Location/Qualifiers
misc_feature            1..33
                        note = Primer Oligonucleotide
source                  1..33
                        mol_type = other DNA
                        organism = synthetic construct
SEQUENCE: 51
cacctacaga gaaacaaatt cctactggca ccc                                33

SEQ ID NO: 52           moltype = DNA  length = 60
FEATURE                 Location/Qualifiers
misc_feature            1..60
                        note = Primer Oligonucleotide
source                  1..60
                        mol_type = other DNA
                        organism = synthetic construct
SEQUENCE: 52
ttggcggtct atagatacct tggttatggc gcccgtcgac aactaaactg gaatgtgagg   60

SEQ ID NO: 53           moltype = DNA  length = 60
FEATURE                 Location/Qualifiers
misc_feature            1..60
                        note = Primer Oligonucleotide
source                  1..60
                        mol_type = other DNA
                        organism = synthetic construct
SEQUENCE: 53
acttttgttg ttccctcaca ttccagttta gttgtcgacg ggcgccataa ccaaggtatc   60

SEQ ID NO: 54           moltype = DNA  length = 60
FEATURE                 Location/Qualifiers
misc_feature            1..60
                        note = Primer Oligonucleotide
source                  1..60
                        mol_type = other DNA
                        organism = synthetic construct
SEQUENCE: 54
ccaacaaaga aacccaagta gccaagtttt gagacaacat gtttagttaa ttatagttcg   60

SEQ ID NO: 55           moltype = DNA  length = 59
FEATURE                 Location/Qualifiers
misc_feature            1..59
                        note = Primer Oligonucleotide
source                  1..59
                        mol_type = other DNA
                        organism = synthetic construct
SEQUENCE: 55
gaatatacgg tcaacgaact ataattaact aaacatgttg tctcaaaact tggctactt    59

SEQ ID NO: 56           moltype = DNA  length = 60
FEATURE                 Location/Qualifiers
misc_feature            1..60
                        note = Primer Oligonucleotide
source                  1..60
                        mol_type = other DNA
                        organism = synthetic construct
SEQUENCE: 56
aaatgaaaaa aaagtggta gattgggcta cgtaaattcg atcaagcgtt gaattgtctg    60

SEQ ID NO: 57           moltype = DNA  length = 60
FEATURE                 Location/Qualifiers
```

```
misc_feature      1..60
                  note = Primer Oligonucleotide
source            1..60
                  mol_type = other DNA
                  organism = synthetic construct
SEQUENCE: 57
gctttgaacg acagaagata cagacaattc aacgcttgat cgaatttacg tagcccaatc  60

SEQ ID NO: 58     moltype = DNA  length = 60
FEATURE           Location/Qualifiers
misc_feature      1..60
                  note = Primer Oligonucleotide
source            1..60
                  mol_type = other DNA
                  organism = synthetic construct
SEQUENCE: 58
attttgaggg aaggggggaag attgtagtac ttttcgagaa caaatgacgt caaagaagt  60

SEQ ID NO: 59     moltype = DNA  length = 60
FEATURE           Location/Qualifiers
misc_feature      1..60
                  note = Primer Oligonucleotide
source            1..60
                  mol_type = other DNA
                  organism = synthetic construct
SEQUENCE: 59
taggctcata taatacttct tttgacgtca tttgttctcg aaaagtacta caatcttccc  60

SEQ ID NO: 60     moltype = DNA  length = 44
FEATURE           Location/Qualifiers
misc_feature      1..44
                  note = Primer Oligonucleotide
source            1..44
                  mol_type = other DNA
                  organism = synthetic construct
SEQUENCE: 60
gaacttctgc ctttgaacaa tttcccaaac aattttcatt ggtc                   44
```

LIMITING YEAST-PRODUCED TREHALOSE IN FERMENTATION

CROSS-REFERENCE TO RELATED APPLICATIONS AND DOCUMENTS

This application claims priority from U.S. provisional patent application 62/251,885 filed on Nov. 6, 2015. This application is filed concurrently with a sequence listing in an electronic format. The content of the priority application and the sequence listing is herewith incorporated in its entirety.

REFERENCE TO AN ELECTRONIC SEQUENCE LISTING

The contents of the electronic sequence listing (580127_418C4_SEQUENCE_LISTING.xml; Size: 87081 bytes; and Date of Creation: Feb. 25, 2023) is herein incorporated by reference in its entirety.

TECHNOLOGICAL FIELD

This disclosure relates to the use of recombinant yeast host cells for limiting the production and/or secretion of trehalose during fermentation, such as, for example, an alcoholic fermentation. The use of the recombinant yeast host cells can increase the production of one or more fermentation product, such as, for example, ethanol.

BACKGROUND

*Saccharomyces cerevisiae* is the primary biocatalyst used in the commercial production of fuel ethanol. This organism is proficient in fermenting glucose to ethanol, often to concentrations greater than 20% w/v. However, *S. cerevisiae* lacks the ability to hydrolyze polysaccharides and therefore may require the exogenous addition of enzymes to convert complex sugars to glucose. Several *S. cerevisiae* strains have been genetically engineered to express alpha(α)-amylase and/or glucoamylase (see for example, WO 2011/153516 and WO 2012/138942) and the use of such strains increases the overall yield while representing a substantial cost savings.

One potential for yield improvements is targeting the breakdown of residual fermentable sugars. For example, a typical corn ethanol fermentation will have approximately 4 g/L of residual disaccharide sugars (also referred to as degree of polymerization 2 or DP2), comprised of maltose, isomaltose and the majority being trehalose (Giffen 2012). These disaccharides represent a potential of an additional 4 g/L ethanol.

Trehalose is a non-reducing disaccharide composed of two glucose molecules linked at the 1-carbon, forming an α-α bond. In yeasts, trehalose can act as carbohydrate storage, but more importantly, it has been well characterized to act as a stress protectant against desiccation, high temperatures, ethanol toxicity, and acidic conditions by stabilizing biological membranes and native proteins (Elbein et al. 2003; Singer and Lindquist 1998). Intracellular trehalose is well-regulated in yeast based on an equilibrium between synthesis and degradation. It is obtained by catalyzing the combination of a uridine-diphosphate-glucose moiety to a glucose-6-phosphate to form trehalose-6-phosphate (see FIG. 1). The phosphate group is then removed to form trehalose. The primary pathway is facilitated by a protein complex encoded by four genes: the trehalose-6-phosphate synthase (TPS1 encoded by the tps1 gene), trehalose-6-phosphate phosphatase (TPS2 encoded by the tps2 gene) and two regulatory proteins, TPS3 and TSL1. Trehalose can be catabolized into two glucose molecules by either the cytoplasmic trehalase enzyme, NTH1, or the tethered, extracellular trehalase, ATH1. Under certain conditions, trehalose can also be excreted from the yeast.

The trehalose biosynthetic pathway has also been proposed to be a primary regulator of glycolysis by creating a futile cycle. As glucose is phosphorylated by hexokinase (HXK), the intracellular free organic phosphate levels are quickly depleted which is required for downstream processes and other metabolic processes (see FIG. 1). Conversion of glucose-6-phosphate into trehalose not only removes the sugar from glycolysis, creating a buffer, but the pathway also regenerates inorganic phosphate. Another primary control of glycolysis is the inhibition of HXK2 by trehalose-6-phosphate, thereby further slowing the glycolysis flux.

Numerous manipulations of the trehalose pathway in *S. cerevisiae* have been reported. Attempts at trehalose manipulations as a means of targeting ethanol yield increases have primarily focused on over-expression of the pathway, particularly with TPS1/TPS2 (Cao et al. 2014; Guo et al. 2011; An et al. 2011). Ge et al. (2013) successfully improved ethanol titers on pure glucose with the over-expression of the TSL1 component, which has also been implicated in glucose signaling. Deletion of the biosynthetic pathway has proved more challenging. As reviewed by Thevelein and Hohmann (1995), attempts to remove the TPS1 function have led to the decreased ability to grow on readily fermentable carbon sources due to the aforementioned control of glycolysis. Functional analysis of the TPS complex has been extensively studied using knockout approaches (Bell et al. 1998), but none have targeted deletion of the key biosynthetic genes as a means of improving ethanol yields nor have they targeted relevant fuel ethanol processes.

It would be highly desirable to be provided with methods of using recombinant yeast host cells which are capable of modulating the production and/or the excretion of trehalose and/or trehalose breakdown while being capable of fermenting a medium and producing a fermentation product.

BRIEF SUMMARY

The present disclosure relates to the use of recombinant yeasts capable of limiting the accumulation of trehalose during fermentation in order to increase the production of another fermentation product during fermentation. The recombinant yeast host cells comprises at least two genetic modifications. The first genetic modification allows for reducing the production of one or more native enzymes that function to produce glycerol or regulating glycerol synthesis and/or allowing the production of an heterologous glucoamylase. The second genetic modification allows for reducing the production of one or more native enzymes that function to produce or regulating trehalose synthesis and/or allowing the expression of an heterologous trehalase.

In a first aspect, the present disclosure provides a recombinant yeast host cell comprising: (i) a first genetic modification for reducing the production of one or more native enzymes that function to produce glycerol or regulating glycerol synthesis and/or allowing the production of an heterologous glucoamylase; and (ii) a second genetic modification for reducing the production of one or more native enzymes that function to produce trehalose or regulating trehalose synthesis and/or allowing the expression of an heterologous trehalase. In an embodiment, the recombinant yeast host cell has the second genetic modification allowing the expression of the heterologous trehalase. In an embodiment, the recombinant yeast host cell has the first genetic modification for reducing the production of the one or more native enzymes that function to produce glycerol and the second genetic modification for reducing the production of the one or more native enzymes that function to produce trehalose or regulating trehalose synthesis. In another embodiment, the recombinant yeast host cell has the first modification for reducing the production of the one or more native enzymes that function to produce glycerol or regulating glycerol synthesis and the second modification allowing the production of the heterologous trehalase. In yet another embodiment, the recombinant yeast host cell has the first genetic modification allowing the production of the heterologous glucoamylase and the second genetic modification for reducing the production of the one or more native enzymes that function to produce trehalose or regulating trehalose synthesis. In still another embodiment, the recombinant yeast host cell has the first genetic modification allowing the production of the heterologous glucoamylase and the second genetic modification allowing the production of the heterologous trehalase. In a further embodiment, the recombinant yeast host cell comprises a further (third) genetic modification for reducing the production of the one or more native enzymes that function to catabolize formate. In such embodiment, the recombinant yeast host cell can, for example, lack the ability to produce a FDH1 polypeptide and/or a FDH2 polypeptide. In an embodiment, the recombinant yeast host cell comprises a further (fourth) genetic modification to reduce the production of the one or more native enzymes that function to produce glycerol (e.g., decreases or inhibits in the expression of the a GPD1 polypeptide and/or a GPD2 polypeptide) or regulating glycerol synthesis (e.g., decreases or inhibits the expression of a FPS1 polypeptide and/or increases the expression of a STL1 polypeptide). In another embodiment, the recombinant yeast host cell comprises a further (fifth) genetic modification allowing the expression of heterologous glucoamylase. In an embodiment, the heterologous glucoamylase is from the genus *Saccharomycopsis* sp., such as, for example, from the species *Saccharomycopsis fibuligera*. In yet a further embodiment, the heterologous glucoamylase has or consists of the amino acid sequence of SEQ ID NO: 3, is a variant of the amino acid sequence of SEQ ID NO: 3 or is a fragment of the amino acid sequence of SEQ ID NO: 3. In another embodiment, the second genetic mutation causes a reduction in the expression level or prevents the expression of the one or more native enzymes that function to produce trehalose or regulating trehalose synthesis, such as, for example, the TPS2 polypeptide or a polypeptide encoded by a tps2 ortholog. In a further embodiment, the heterologous trehalase is an acid trehalase. In a further embodiment, the acid trehalase is from the genus *Aspergillus* sp., for example, from the species *Aspergillus fumigatus* or the species *Aspergillus nidulans*. In an embodiment, the acid trehalase has the amino acid sequence of SEQ ID NO: 1, is a variant of the amino acid sequence of SEQ ID NO: 1 or is a fragment of the amino acid sequence of SEQ ID NO: 1. In yet another embodiment, the acid trehalase has the amino acid sequence of SEQ ID NO: 2, is a variant of the amino acid sequence of SEQ ID NO: 2 or is a fragment of the amino acid sequence of SEQ ID NO: 2. In still another embodiment, the recombinant yeast host cell is from the genus *Saccharomyces* sp., such as, for example, from the species *Saccharomyces cerevisiae*.

In a second aspect, the present disclosure provides a method of limiting the accumulation of extracellular trehalose during a fermentation. Broadly, the method comprises fermenting a medium with at least one recombinant yeast host cell described herein. In an embodiment, the method can also include adding an heterologous trehalase to the medium.

In a third aspect, the present disclosure provides a method of increasing the production of a fermentation product during a fermentation, said method comprising fermenting a medium with at least one recombinant yeast host cell described herein. In an embodiment, the method can also include adding an heterologous acid trehalase to the medium. In a further embodiment, the fermentation product is ethanol. In yet another embodiment, the medium comprises starch which can be optionally be provided in a gelatinized or a raw form. In yet another embodiment, the medium can be derived from corn. In another embodiment, the medium comprises maltodextrin.

BRIEF DESCRIPTION OF THE DRAWINGS

Having thus generally described the nature of the invention, reference will now be made to the accompanying drawings, showing by way of illustration, a preferred embodiment thereof, and in which.

The M8841+MP244 fermentations received 100 μg/ml of purified MP244. Results are shown as ethanol concentration (in g/L) in function of experimental conditions used.

Figure 5:
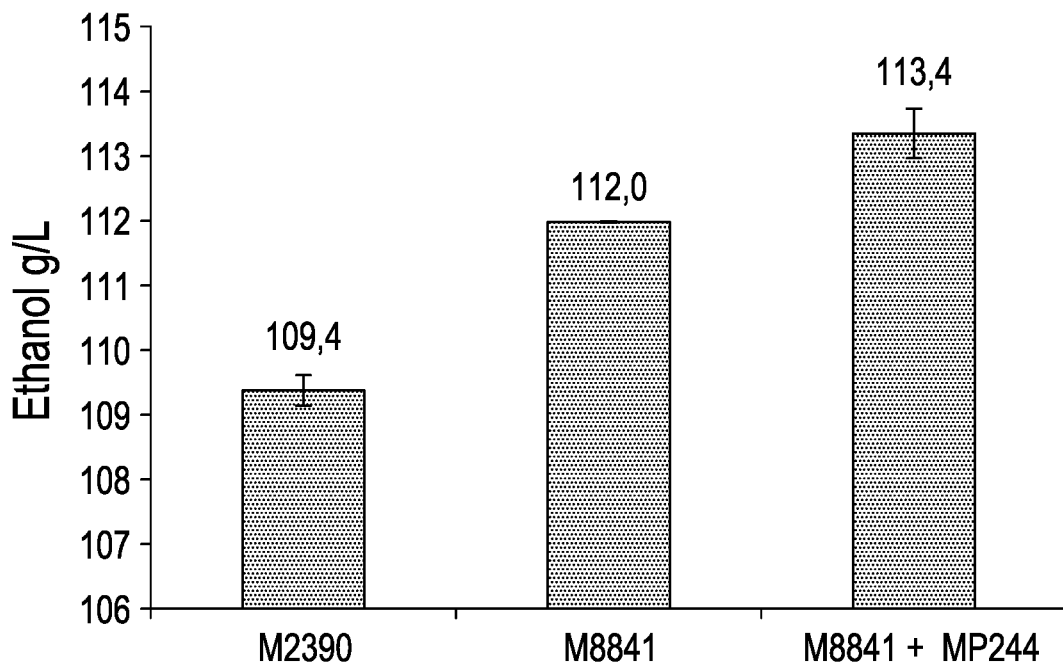
FIG. 5 illustrates the effect of supplementing a fermentation medium with a trehalase on ethanol production. A 25.5% corn mash fermentation was conducted comparing the conventional strain (M2390) to a strain genetically engineered to express a glucoamylase strain (M8841) with and without the addition of purified yeast-made trehalase (MP244). M2390 received a 100% dose of commercial GA, whereas both M8841 treatments received a 50% GA dose.
Figure 6:
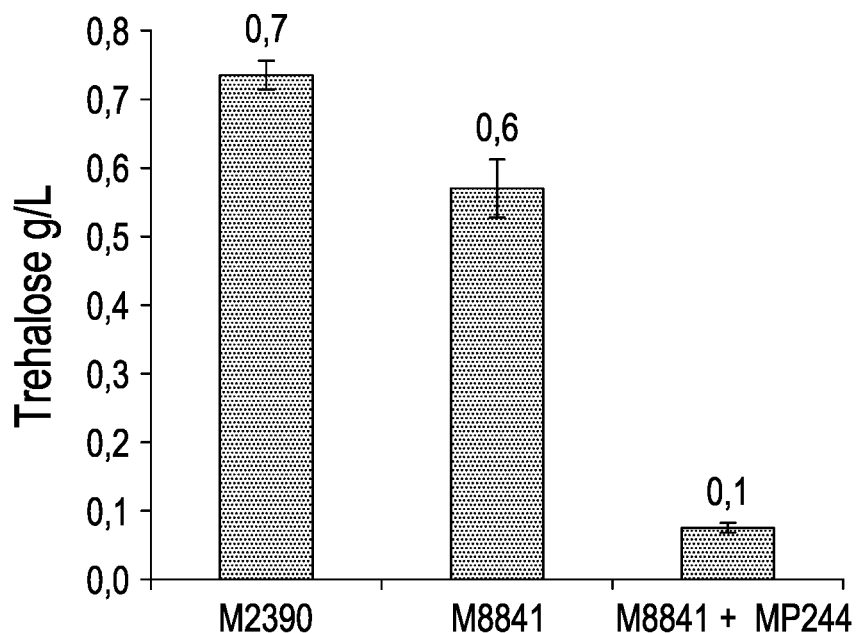

FIG. 6 illustrates the effect of supplementing a fermentation medium with a trehalase on residual trehalose at the end of a 25.5% corn mash fermentation (described in the legend of FIG. 5). Results are shown as trehalose concentration (in g/L) in function of experimental conditions used.

Figure 7A:
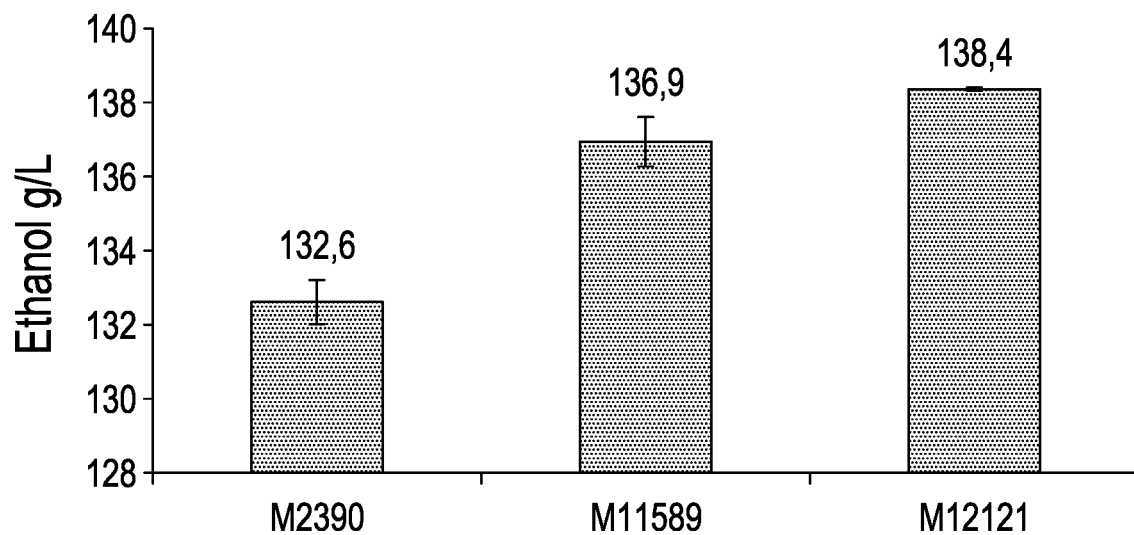
Figure 7B:
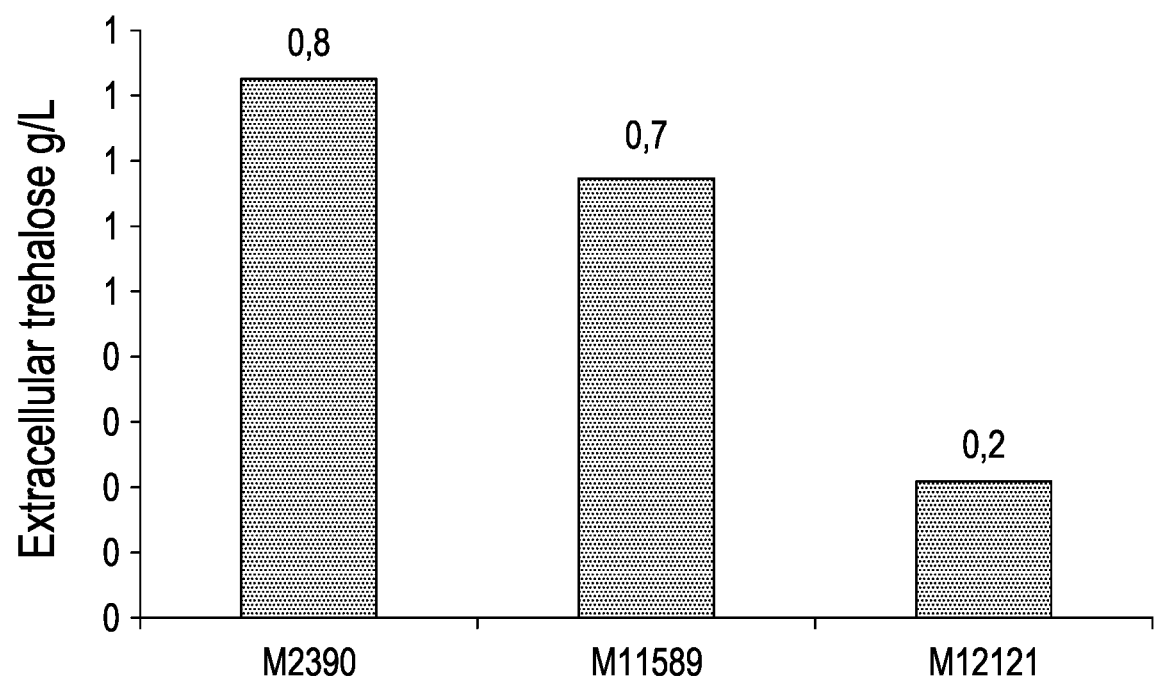

FIGS. 7A and 7B illustrate the effects of fermenting a fermentation medium by a S. cerevisiae strain expressing an heterologous glucoamylase and an heterologous trehalase on ethanol production (A) and trehalose concentration (B). Results are shown as ethanol concentration (A, in g/L) or trehalose concentration (B, in g/L) in function of experimental conditions used.

FIG. 8A to 8E illustrate the genetic maps of the different cassettes used to generate some of the recombinant yeast strains of the Examples. (A) Map of the MA613 cassette used for making the M4652 strain. KT-MX and NT-MX cassette used to knock-out the tps1 open reading frame. The cassette contains the positive selection markers kanamycin gene or nourseothricin gene under control of the Ashbya gossypii tef promoter and terminator along with the HSV-thymidine kinase negative selection marker under control of the S. cerevisiae hxt2 promoter and act1 terminator. (B) Map of the MA614 cassette used for making the M4653 strain. KT-MX and NT-MX cassette used to knock-out the tps2 open reading frame. The cassette contains the positive selection markers kanamycin gene or nourseothricin gene under control of the Ashbya gossypii tef promoter and terminator along with the HSV-thymidine kinase negative selection marker under control of the S. cerevisiae hxt2 promoter and act1 terminator. (C) Map of the MA1920 cassette for making the M11245 strain and integrating the MP244 trehalase at the FCY1 locus under control of the native S. cerevisiae tef2 promoter and adh3 terminator. (D) Map of the MAP516 cassette for making the M10957 strain and for integrating the MP848 trehalase at the FCY1 locus under control of the native S. cerevisiae tef2 promoter and idp1 terminator. (E) Map of the MAP811 cassette for making the M12121 and M13913 strains and for integrating MP244 trehalase at the IME1 locus under control of the native S. cerevisiae tef2 promoter and idp1 terminator.

Figure 9A:
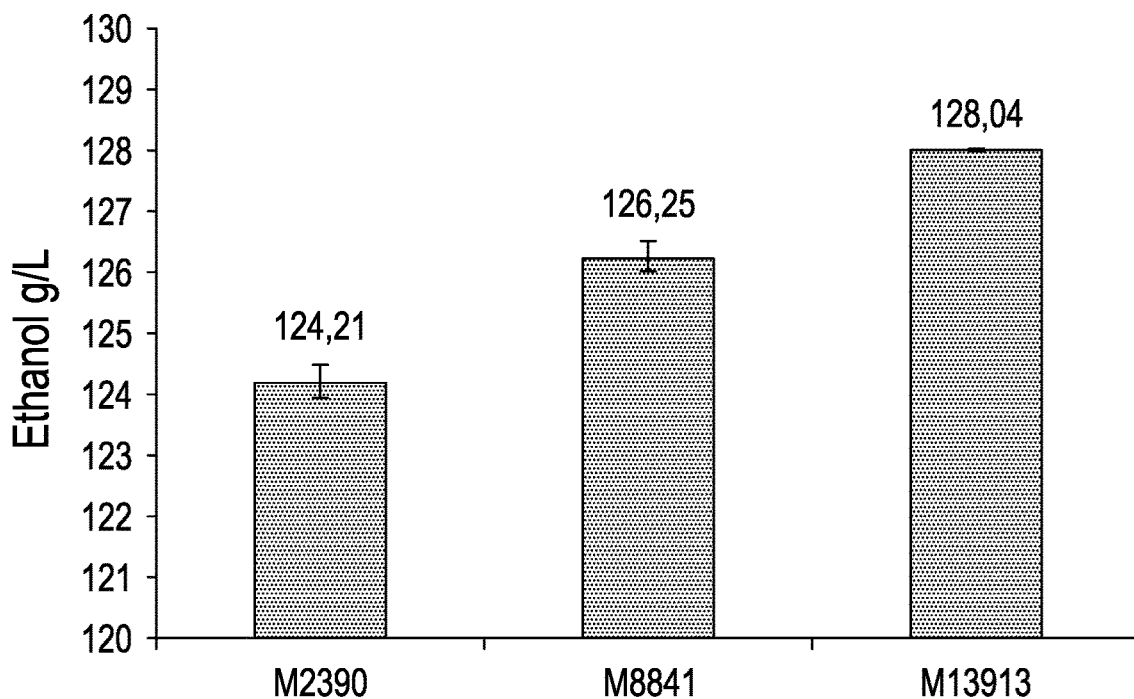
Figure 9B:
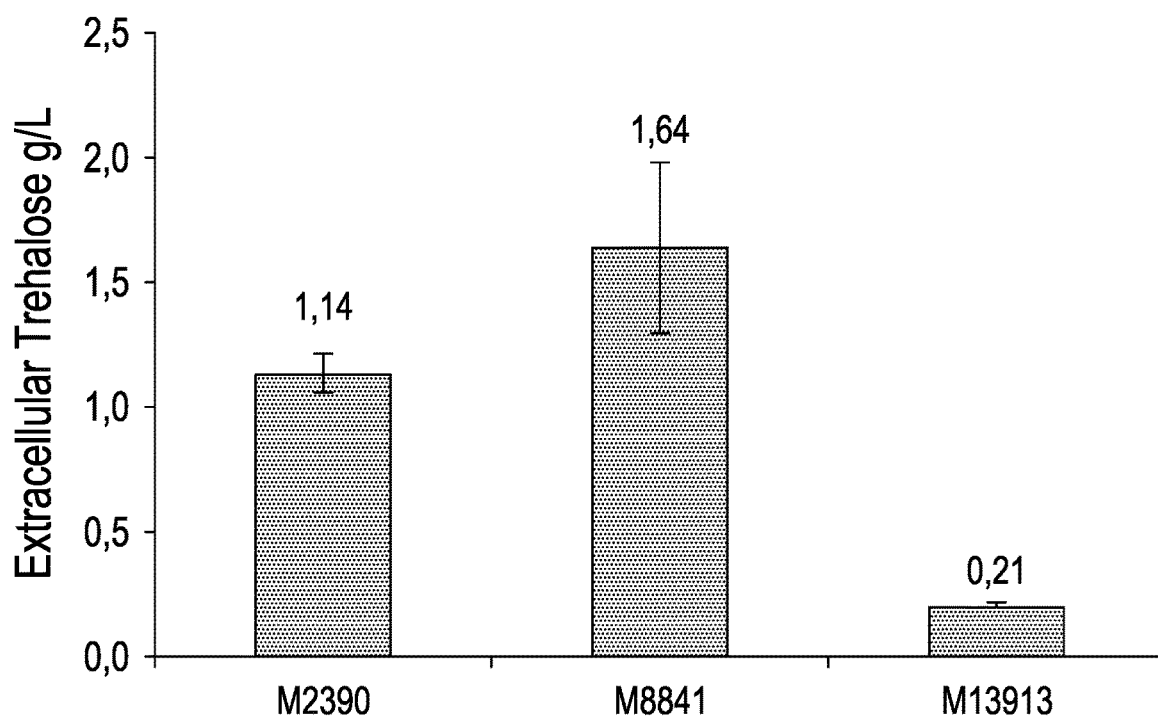

FIGS. 9A and 9B illustrate the effects of a maltodextrin fermentation by a S. cerevisiae strain M13913 expressing an heterologous glucoamylase, the glycerol reduction pathway as described in WO 2012/138942 and an heterologous trehalase on ethanol (A) and trehalose (B) concentrations. Results are shown as ethanol concentration (A, in g/L) or trehalose concentration (B, in g/L) in function of experimental conditions used.

DETAILED DESCRIPTION

The present disclosure relates to the use of recombinant yeast host cells capable of limiting the production, accumulation or excretion of trehalose during fermentation. The recombinant yeast host cell comprising at least two distinct genetic modifications (also referred to as genetic mutations). The genetic modifications are preferably made using genetic engineering techniques. Firstly, the recombinant yeast host cells can be modified to reduce or inhibit the production of one or more native enzymes that function to produce glycerol or regulating glycerol synthesis. Alternatively or in combination, the recombinant yeast host cells can be modified to produce an heterologous glucoamylase. Secondly, the recombinant yeast host cells can be modified to reduce or inhibit the production of one or more native enzymes that function to produce trehalose or regulating trehalose synthesis. Alternatively or in combination, the recombinant yeast host cells can be modified to produce an heterologous trehalase. The use of such recombinant yeast host cells, in some conditions, limits the level of trehalose during fermentation to a maximum of 1.0 g/L.

Recombinant Yeast Host Cells

The present disclosure concerns recombinant yeast host cells that have been genetically engineered to include at least two genetic modifications. The genetic modifications can be made in one or both copies of the targeted gene(s). In the context of the present disclosure, when recombinant yeast cell is qualified as being "genetically engineered", it is understood to mean that it has been manipulated to either add at least one or more heterologous or exogenous nucleic acid residue and/or removed at least one endogenous (or native) nucleic acid residue. The genetic manipulations did not occur in nature and are the results of in vitro manipulations of the yeast.

In the context of the present disclosure, the recombinant host cell is a yeast. Suitable yeast host cells can be, for example, from the genus Saccharomyces, Kluyveromyces, Arxula, Debaryomyces, Candida, Pichia, Phaffia, Schizosaccharomyces, Hansenula, Kloeckera, Schwanniomyces or Yarrowia. Suitable yeast species can include, for example, S. cerevisiae, S. bulderi, S. barnetti, S. exiguus, S. uvarum, S. diastaticus, K. lactis, K. marxianus or K. fragilis. In some embodiments, the yeast is selected from the group consisting of Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe and Schwanniomyces occidentalis. In one particular embodiment, the yeast is Saccharomyces cerevisiae. In some embodiment, the host cell can be an oleaginous yeast cell. For example, the oleaginous yeast host cell can be from the genus Blakeslea, Candida, Cryptococcus, Cunninghamella, Lipomyces, Mortierella, Mucor, Phycomyces, Pythium, Rhodosporidum, Rhodotorula, Trichosporon or Yarrowia. In some alternative embodiment, the host cell can be an oleaginous microalgae host cell (e.g., for example, from the genus Thraustochytrium or Schizochytrium). In an embodiment, the recombinant yeast host cell is from the genus Saccharomyces and, in some embodiments, from the species Saccharomyces cerevisiae.

The first modification of the recombinant yeast host cell can be a genetic modification leading to the reduction in the production, and in an embodiment to the inhibition in the production, of one or more native enzymes that function to produce glycerol or regulating glycerol synthesis. As used in the context of the present disclosure, the expression "reducing the production of one or more native enzymes that function to produce glycerol or regulating glycerol synthesis" refers to a genetic modification which limits or impedes the expression of genes associated with one or more native polypeptides (in some embodiments enzymes) that function to produce glycerol or regulating glycerol synthesis, when compared to a corresponding yeast strain which does not bear the first genetic modification. In some instances, the first genetic modification reduces but still allows the production of one or more native polypeptides that function to produce glycerol or regulating glycerol synthesis. In other instances, the first genetic modification inhibits the production of one or more native enzymes that function to produce glycerol or regulating glycerol synthesis. In some embodiments, the recombinant yeast host cells bear a plurality of first genetic modifications, wherein at least one reduces the production of one or more native polypeptides and at least another inhibits the production of one or more native polypeptides. As used in the context of the present disclosure, the expression "native polypeptides that function to produce glycerol or regulating glycerol synthesis" refers to polypeptides which are endogenously found in the recombinant yeast host cell. Native enzymes that function to produce glycerol include, but are not limited to, the GPD1 and the GPD2 polypeptide (also referred to as GPD1 and GPD2 respectively). Native enzymes that function to regulating glycerol synthesis include, but are not limited to, the FPS1 polypeptide as well as the STL1 polypeptide. The FPS1 polypeptide is a glycerol exporter and the STL1 polypeptide functions to import glycerol in the recombinant yeast host cell. By either reducing or inhibiting the expression of the FPS1 polypeptide and/or increasing the expression of the STL1 polypeptide, it is possible to control, to some extent, glycerol synthesis. In an embodiment, the recombinant yeast host cell bears a genetic modification in at least one of the gpd1 gene (encoding the GPD1 polypeptide), the gpd2 gene (encoding the GPD2 polypeptide), the fps1 gene (encoding the FPS1 polypeptide) or orthologs thereof. In another embodiment, the recombinant yeast host cell bears a genetic modification in at least two of the gpd1 gene (encoding the GPD1 polypeptide), the gpd2 gene (encoding the GPD2 polypeptide), the fps1 gene (encoding the FPS1 polypeptide) or orthologs thereof. In still another embodiment, the recombinant yeast host cell bears a genetic modification in each of the gpd1 gene (encoding the GPD1 polypeptide), the gpd2 gene (encoding the GPD2 polypeptide) and the fps1 gene (encoding the FPS1 polypeptide) or orthologs thereof. Examples of recombinant yeast host cells bearing such genetic modification(s) leading to the reduction in the production of one or more native enzymes that function to produce glycerol or regulating glycerol synthesis are described in WO 2012/138942. Preferably, the recombinant yeast host cell has a genetic modification (such as a genetic deletion or insertion) only in one enzyme that functions to produce glycerol, in the gpd2 gene, which would cause the host cell to have a knocked-out gpd2 gene. In some embodiments, the recombinant yeast host cell can have a genetic modification in the gpd1 gene, the gpd2 gene and the fps1 gene resulting is a recombinant yeast host cell being knock-out for the gpd1 gene, the gpd2 gene and the fps1 gene. In still another embodiment (in combination or alternative to the "first" genetic modification described above), the recombinant yeast host cell can have a genetic modification in the stl1 gene (e.g., a duplication for example) for increasing the expression of the STL1 polypeptide.

The first genetic modification can also allow for the production of an heterologous glucoamylase. Many microbes produce an amylase to degrade extracellular starches. In addition to cleaving the last α(1-4) glycosidic linkages at the non-reducing end of amylose and amylopectin, yielding glucose, γ-amylase will cleave α(1-6) glycosidic linkages. The heterologous glucoamylase can be derived from any organism. In an embodiment, the heterologous protein is derived from a γ-amylase, such as, for example, the glucoamylase of Saccharomycoces filbuligera (e.g., encoded by the glu 0111 gene). Examples of recombinant yeast host cells bearing such first genetic modifications are described in WO 2011/153516.

The heterologous glucoamylase can be a variant of a known glucoamylase, for example a variant of the heterologous glucoamylase having the amino acid sequence of SEQ ID NO: 3. The glucoamylase variants have at least 50%, 55%, 60%, 65%, 70%, 75%, 80%, 85%, 90%, 95%, 96%, 97%, 98% or 99% identity to the glucoamylases described herein. A variant comprises at least one amino acid difference when compared to the amino acid sequence of the native glucoamylase. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5. The variant heterologous glucoamylases described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide.

A "variant" of the glucoamylase can be a conservative variant or an allelic variant. As used herein, a conservative variant refers to alterations in the amino acid sequence that do not adversely affect the biological functions of the glucoamylase. A substitution, insertion or deletion is said to adversely affect the protein when the altered sequence prevents or disrupts a biological function associated with the glucoamylase (e.g., the hydrolysis of starch). For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the glucoamylase.

The heterologous glucoamylase can be a fragment of a known glucoamylase or fragment of a variant of a known glucoamylase (such as, for example, a fragment of the glucoamylase having the amino acid sequence of SEQ ID NO: 3). Glucoamylase "fragments" have at least at least 100, 200, 300, 400, 500 or more consecutive amino acids of the glucoamylase. A fragment comprises at least one less amino acid residue when compared to the amino acid sequence of the glucoamylase and still possess the enzymatic activity of the full-length glucoamylase. In some embodiments, fragments of the glucoamylases can be employed for producing the corresponding full-length glucoamylase by peptide synthesis. Therefore, the fragments can be employed as intermediates for producing the full-length proteins.

The heterologous nucleic acid molecule encoding the heterologous glucoamylase, variant or fragment can be integrated in the genome of the yeast host cell. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies in the yeast host cell's genome. Alternatively, the heterologous nucleic acid molecule can be independently replicating from the yeast's genome. In such embodiment, the nucleic acid molecule can be stable and self-replicating.

In the context of the present disclosure, the recombinant yeast host cell can include at least two "first" genetic modifications, one in leading to the reduction in the production of one or more native enzymes that function to produce glycerol or regulating glycerol synthesis and another one leading to the expression of an heterologous glucoamylase. It is also contemplated that the recombinant yeast host cell can include a single first genetic modification, either for reducing in the production of one or more native enzymes that function to produce glycerol or regulating glycerol synthesis or for expressing an heterologous glucoamylase.

The second genetic modification of the recombinant yeast host cell can lead to the reduction in the production (or the prevention of expression) of one or more native enzymes that function to produce trehalose or regulating trehalose synthesis. As used in the context of the present disclosure, the expression "reducing the production of one or more native enzymes that function to produce trehalose or regulating trehalose synthesis" refers to a genetic modification which limits or impedes the expression of genes associated with one or more native polypeptides (in some embodiments enzymes) that function to produce trehalose or regulating trehalose synthesis, when compared to a corresponding yeast strain which does not bear the second genetic modification. In some instances, the second genetic modification reduces but still allows the production of one or more native polypeptides that function to produce trehalose or regulating trehalose synthesis. In other instances, the second genetic modification inhibits the production of one or more native enzymes that function to produce trehalose or regulating trehalose synthesis. In some embodiments, the recombinant yeast host cells bear a plurality of second genetic modifications, wherein at least one reduces the production of one or more native polypeptides and at least another inhibits the production of one or more native polypeptides. As used in the context of the present disclosure, the expression "native polypeptides that function to produce trehalose or regulating trehalose synthesis" refers to polypeptides which are endogenously found in the recombinant yeast host cell. Native enzymes that function to produce trehalose include, but are not limited to, the TPS1 and TPS2 (both members of the TPS complex). Native enzymes that function to regulating trehalose synthesis include, but are not limited to polypeptides involved in interacting with the TPS complex such as, for example, TPS3 and TSL1 as well as polypeptides responsible for synthesizing precursors of the TPS complex such as, for example, NTH1, NTH2, ATH1, HXK1, HXK2, GLK1, PGM1, PGM2, GPH1, UGP1, GSY1 and GSY2. In an embodiment, the recombinant yeast host cell bears a genetic modification in at least one, two, three or more of the tps1 gene (encoding the TPS1 polypeptide), the tps2 gene (encoding the TPS2 polypeptide), the tps3 gene (encoding the TPS3 polypeptide), the tsl1 gene (encoding the TSL1 polypeptide), the nth1 gene (encoding the NTH1 polypeptide), the nth2 gene (encoding the NTH2 polypeptide), the ath1 gene (encoding the ATH1 polypeptide), the hxk1 gene (encoding the HXK1 polypeptide), the hxk2 gene (encoding the HXK2 polypeptide), the g/k1 gene (encoding the GLK1 polypeptide), the pgm1 gene (encoding the PGM1 polypeptide), the pgm2 gene (encoding the PGM2 polypeptide), the gph1 gene (encoding the GPH1 polypeptide), the ugp1 gene (encoding the UGP1 polypeptide), the gsy1 gene (encoding the GSY1 polypeptide), the gsy2 gene (encoding the GSY2 polypeptide) or orthologs thereof. Preferably, the recombinant yeast host cell has a genetic modification (such as a genetic deletion or insertion) only in one enzyme that functions to produce glycerol, in the tps2 gene, which would cause the host cell to have a knocked-out tps2 gene.

In some circumstances, the second genetic modification can be made to (or, in some instances, limited to) the tps2 gene or to the tps2 gene ortholog. As such, the recombinant yeast host cell can lack the ability to produce a biologically active trehalose-6-phosphate phosphatase (TPS2 polypeptide). The yeast strain can be genetically engineered to impede or prevent the expression of the tps2 gene or to allow the expression of a non-functional TPS2 polypeptide. In an embodiment, the second genetic modification can be limited to the tps2 gene (or its ortholog), its corresponding transcript or its corresponding polypeptide and are intended to either reduce the expression of the gene, reduce the expression and/or stability of the transcript, reduce the expression and/or stability of the polypeptide or reduce the biological activity of the polypeptide. In one embodiment, the open-reading frame of the tps2 gene (or its ortholog) is disrupted specifically by the introduction of an heterologous nucleic acid molecule. In another embodiment, the open-reading frame of the tps2 gene can be deleted (in part or in total).

In some instances, the recombinant yeast host cell can have the ability to produce trehalose-6-phosphate (for example by producing the TPS1 polypeptide). In the context of the present disclosure, the expression "capable of producing trehalose-6-phosphate" refers to a yeast strain which has the ability of expressing a gene or a combination of genes leading to the production of trehalose-6-phosphate. The trehalose-6-phosphate synthase gene (also referred to the tps1 gene) and the activity of the trehalose-6-phosphate synthase (referred to as the TPS1 polypeptide) are important in the production of trehalose-6-phosphate. As such, a recombinant yeast strain capable of producing trehalose-6-phosphate usually has a tps1 gene and is capable of expressing a functional/biologically active TPS1 polypeptide. As it is known in the art, the TPS1 polypeptide is an enzyme involved in the synthesis of trehalose-6-phosphate from UDP-glucose.

Still in the context of the present disclosure, the expression "lacking the ability to produce a biologically active trehalose-6-phosphate phosphatase (TPS2 polypeptide)" refers to a yeast strain which has been genetically engineered to prevent the expression from the tps2 gene or expresses a non-functional trehalose-6-phosphate phosphatase (TPS2 polypeptide). As known in the art, the tps2 gene encodes an enzyme (TPS2 polypeptide) having the ability to recognize trehalose-6-phosphate and cleave the bound between trehalose and the phosphate group. As such, a biologically active or functional TPS2 polypeptide is capable of recognizing trehalose-6-phosphate and cleave the bound between trehalose and the phosphate group. It follows that a biologically inactive or non-functional TPS2 polypeptide cannot recognize trehalose-6-phospate and/or cleave the bound between trehalose and the phosphate group.

As indicated above, the recombinant yeast host cell can be genetically engineered to impede or prevent the expression of the tps2 gene (or a tps2 gene ortholog) by manipulating the endogenous coding sequence of the nucleic acid sequence of the tps2 gene (or the tps2 gene ortholog). The tps2 gene (also known as hog2 or pfk3) has been specifically described in Saccharomyces cerevisiae and is associated with the Gene ID 851646. In the context of the present disclosure, a "tps2 gene ortholog" is understood to be a gene in a different species that evolved from a common ancestral gene by speciation. In the context of the present invention, a tps2 ortholog retains the same function, e.g. it encodes for an enzyme capable of dephosphorylating trehalose-6-phosphate.

The TPS2 polypeptide has been specifically described in Saccharomyces cerevisiase under GenBank Accession Number CAA98893.1. In the context of the present disclosure, the tps2 gene (or its ortholog) can encode a TPS2 polypeptide having one of the following GenBank Accession Number XP_009255856.1, CEP23739.1, EKJ75382.1, CAA98893.1, P31688.3 GI:1730010, 014145.1, NP_010359.1, DAA11920.1, CAB16285., NP_594975.1, CAA86796.1, AAF80562.1, CAA50025.1, CDM32404.1, BA038481.1, AJV20879.1, AJV20163.1, AJV19466.1, AJV18745.1, AJV18033.1, AJV17324.1, AJV16619.1, AJV15908.1, AJV15200.1, AJV14492.1, AJV13824.1, AJV13114.1, AJV12465.1, AJV11777.1, AJV11078.1, AJV10431.1, AJV09728.1, AJV09023.1, AJV08338.1, AJV07644.1, AJV06938.1, AJV06235.1, AJV05531.1, AJV04812.1, AJV04100.1, AJV03395.1, AJV02725.1, AJV02019.1, AJV01306.1, AJV00594.1, AJU99880.1, AJU99185.1, AJU98485.1, AJU97772.1, AJU97074.1, AJU96370.1, AJU95666.1, AJU94967.1, AJU94268.1, AJU93563.1, AJU92846.1, AJU92131.1, AJU91414.1, AJU90697.1, AJU89979.1, AJU89269.1, AJU88578.1, AJU87873.1, AJU87202.1, AJU86553.1, AJU85852.1, AJU85155.1, AJU84444.1, AJU83731.1, AJU83018.1, AJU82439.1, AJU81736.1, AJU81046.1, AJU80346.1, AJU79746.1, AJU79035.1, AJU78323.1, AJU77611.1, AJU76901.1, AJU76191.1, AJU75483.1, AJU74777.1, AJU74061.1, AJU73348.1, AJU72635.1, AJU71925.1, AJU71213.1, AJU70526.1, AJU69816.1, AJU69121.1, AJU68429.1, AJU67713.1, AJU66996.1, AJU66318.1, AJU65601.1, AJU64885.1, AJU64173.1, AJU63483.1, AJU62784.1, AJU62085.1, AJU61373.1, AJU60685.1, AJU60022.1, AJU59308.1, AJU58621.1, AJU57919.1, AJP37799.1, AHY75069.1, EGW34937.1, ABN67480.2, XP_007372349.1, EWG97048.1, ACB46526.1, XP_001385509.2, ACY82596.1, ACY82595.1, EEU05123.1, EDN60419.1, DAA05785.1, CAC17748.1, XP_013021409.1, XP_013017766.1, KMK60772.1, EPY53152.1, EPX75323.1 GI:528065761, EEB06603.1, XP_002172896.1, KEY78745.1, EXX70387.1, EXX62686.1, EXX62685.1, EXX62684.1, EXX62683.1, GAA85661.1, XP_755036.1 or CAD24957.1.

Various methods are known to those skilled in the art to impede or prevent the expression of the endogenous tps2 gene or the endogenous tps2 gene ortholog. In the context of the present disclosure, a gene which is "endogenous" to a yeast is understood to mean that such gene is natively provided in the organism. For example, a gene encoding a TPS2 polypeptide having phosphatase activity is considered endogenous to yeast has been natively produced by such yeast and is not the result of an in vitro genetic modification. As an another example, a gene is considered to be endogenous to a yeast is considered to have been natively included in or produced by such yeast and was not deliberately introduced by genetic means in the yeast.

In order to impede or prevent the expression of the tps2 gene or its ortholog, the recombinant yeast strain can be genetically engineered to disrupt the open-reading frame of the endogenous tps2 gene or its ortholog by inserting a non-coding sequence or adding one or more nucleic acid residues from the open-reading frame. In such instance, while a section of the tps2 gene or of the tps2 gene ortholog could be expressed (for example, the section of the gene which precedes the insertion or addition) but a functional TPS2 polypeptide could not be produced (due to the presence of a non-coding sequence or an addition interrupting the translation of the full-length TPS2 polypeptide). Alternatively (or in combination), the recombinant yeast strain can be genetically-engineered to remove a part or the totality of the endogenous tps2 gene or ortholog from the yeast's genome. In the context of the present disclosure, a deletion refers to the removal of at least one nucleic acid residue of the tps2 gene. In such instance, while a section of the tps2 gene or its ortholog could be expressed (for example the section (if any) which precedes the deletion) but a functional TPS2 polypeptide could not be produced. In another alternative, the recombinant yeast strain can be genetically-engineered to include one of more nucleic acid residue substitution in the tps2 gene or in the tps2 gene ortholog. The one or more nucleic acid residue substitution can cause the introduction of a stop codon in the open-reading frame of the tps2 gene/ortholog or at least one amino acid substitution in the corresponding polypeptide which will no longer be considered a functional or biologically active TPS2 polypeptide. The recombinant yeast strain can be genetically engineered to impede or prevent the expression of the tps2 gene or its ortholog by manipulating the non-coding sequence (promoter for example) associated with the coding sequence of the tps2 gene. The nucleic acid sequence of the promoter of the tps2 gene can be modified to remove, add and/or substitute at least one nucleic acid residue so as to reduce or prevent the expression of the tps2 gene or its ortholog. The mutation, disruption and/or deletion can be made in one of the copy of the tps2 gene or its ortholog present in the yeast's genome or in both copies of the tps2 gene or its ortholog present in the yeast's genome.

The second genetic modification can be associated with the production of an heterologous trehalase, a trehalase variant or a trehalase fragment (having trehalase activity). In such instance, the genetic manipulation is made to add of an heterologous trehalase-encoding gene (and, optionally, additional non-coding region for facilitating or increasing the expression of the trehalase-encoding gene) and is intended to either provide or increase trehalase activity of the recombinant strain.

As used in the context of the present disclosure, a trehalase is an enzyme capable of hydrolyzing one molecule of trehalose in two molecules of glucose. Trehalases (α,α-trehalose-1-C-glucohydrolase, EC 3.2.1.28) have been reported from many organisms including prokaryotes, plants and animals. At least two-types of trehalases, based on their pH optima, have been characterized: acid trehalases (mostly extracellular, usually associated with the yeast's membrane) and neutral trehalases (usually cytosolic). The recombinant yeast strain of the present disclosure can be genetically engineered to express an acid trehalase, a neutral trehalase or both. In some instances, the heterologous trehalase is produced and transported outside the yeast cell (e.g., extracellular).

The heterologous trehalase(s) expressed by the recombinant yeast strain can be provided from any heterologous organism (yeast, bacteria, plants or animals). The term "heterologous" when used in reference to a nucleic acid molecule (such as a promoter or a coding sequence) or a trehalase refers to a nucleic acid molecule or a trehalase that is not natively found in the host yeast. "Heterologous" also includes a native coding region, or portion thereof, that is removed from the source organism and subsequently reintroduced into the source organism in a form that is different from the corresponding native gene, e.g., not in its natural location in the organism's genome. The heterologous nucleic acid molecule is purposively introduced into the yeast. A "heterologous" nucleic acid molecule or trehalase may be derived from any source, e.g., eukaryotes, prokaryotes, viruses, etc. In an embodiment, the heterologous nucleic acid molecule may be derived from an eukaryote (such as, for example, another yeast) or a prokaryote (such as, for example, a bacteria). The term "heterologous" as used herein also refers to an element (nucleic acid or protein) that is derived from a source other than the endogenous source. Thus, for example, a heterologous element could be derived from a different strain of host cell, or from an organism of a different taxonomic group (e.g., different kingdom, phylum, class, order, family genus, or species, or any subgroup within one of these classifications). The term "heterologous" is also used synonymously herein with the term "exogenous".

The heterologous trehalase can be derived from the genus *Aspergillus* and, in some instances, from the species *Aspergillus fumigatus* or *Aspergillus nidulans*. It is possible to use an heterologous trehalase which does not comprise a tethering region and does not have the ability to associate with the surface of the cell producing same. In some embodiments, the heterologous trehalase has or consists of the amino acid sequence of SEQ ID NO: 1 or 2. For example, the recombinant yeast host cell can be genetically manipulated to express one or more heterologous trehalase genes.

The heterologous trehalase can be a variant of a known trehalase, for example a variant of the trehalase having the amino acid sequence of SEQ ID NO: 1 or 2. The trehalase variants have at least 50%, 55%, 60%, 65%, 70%, 75%, 80%, 85%, 90%, 95%, 96%, 97%, 98% or 99% identity to the trehalases described herein. A variant comprises at least one amino acid difference when compared to the amino acid sequence of the native trehalase. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant heterologous trehalases described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide.

A "variant" of the trehalase can be a conservative variant or an allelic variant. As used herein, a conservative variant refers to alterations in the amino acid sequence that do not adversely affect the biological functions of the trehalase. A substitution, insertion or deletion is said to adversely affect the protein when the altered sequence prevents or disrupts a biological function associated with the trehalase (e.g., the hydrolysis of trehalose into two glucose molecules). For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the trehalase.

The heterologous trehalase can be a fragment of a known trehalase or fragment of a variant of a known trehalase (such as, for example, a fragment of the trehalase having the amino acid sequence of SEQ ID NO: 1 or 2). Trehalase "fragments" have at least at least 100, 200, 300, 400, 500, 600, 700, 800, 900, 1 000 or more consecutive amino acids of the trehalase. A fragment comprises at least one less amino acid residue when compared to the amino acid sequence of the trehalase and still possess the enzymatic activity of the full-length trehalase. In some embodiments, fragments of the trehalases can be employed for producing the corresponding full-length trehalase by peptide synthesis. Therefore, the fragments can be employed as intermediates for producing the full-length proteins.

The heterologous nucleic acid molecule encoding the heterologous trehalase, variant or fragment can be integrated in the genome of the yeast host cell. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies in the yeast host cell's genome. Alternatively, the heterologous nucleic acid molecule can be independently replicating from the yeast's genome. In such embodiment, the nucleic acid molecule can be stable and self-replicating.

The present disclosure also provides nucleic acid molecules for modifying the yeast host cell so as to allow the expression of the heterologous trehalase, variant or fragment. The nucleic acid molecule may be DNA (such as complementary DNA, synthetic DNA or genomic DNA) or RNA (which includes synthetic RNA) and can be provided in a single stranded (in either the sense or the antisense strand) or a double stranded form. The contemplated nucleic acid molecules can include alterations in the coding regions, non-coding regions, or both. Examples are nucleic acid molecule variants containing alterations which produce silent substitutions, additions, or deletions, but do not alter the properties or activities of the encoded trehalases, variants or fragments.

In some embodiments, the nucleic acid molecules encoding the heterologous trehalase and/or glucoamylase, fragment or variant are codon-optimized with respect to the intended recipient recombinant yeast host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized sequences described herein corresponds to between about 0.8 and 1.0, between about 0.8 and 0.9, or about 1.0.

The present disclosure also provides nucleic acid molecules that are hybridizable to the complement nucleic acid molecules encoding the heterologous trehalase, the heterologous glucoamylase as well as variants or fragments. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acid molecules contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived. For hybridizations with shorter nucleic acids, i.e. e., oligonucleotides, the position of mismatches becomes more important, and the length of the oligonucleotide determines its specificity. In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The nucleic acid molecules comprise a coding region for the heterologous trehalase as well as its variants and fragments. A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region. In an embodiment, the coding region can be referred to as an open reading frame. "Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

The nucleic acid molecules described herein can comprise transcriptional and/or translational control regions. "Transcriptional and translational control regions" are DNA regulatory regions, such as promoters, enhancers, terminators, and the like, that provide for the expression of a coding region in a host cell. In eukaryotic cells, polyadenylation signals are control regions.

The heterologous nucleic acid molecule can be introduced in the yeast host cell using a vector. A "vector," e.g., a "plasmid", "cosmid" or "YAC" (yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

In the heterologous nucleic acid molecule, the promoter and the nucleic acid molecule(s) coding for the heterologous protein(s) are operatively linked to one another. In the context of the present disclosure, the expressions "operatively linked" or "operatively associated" refers to fact that the promoter is physically associated to the nucleotide acid molecule coding for the heterologous protein in a manner that allows, under certain conditions, for expression of the heterologous protein from the nucleic acid molecule. In an embodiment, the promoter can be located upstream (5') of the nucleic acid sequence coding for the heterologous protein. In still another embodiment, the promoter can be located downstream (3') of the nucleic acid sequence coding for the heterologous protein. In the context of the present disclosure, one or more than one promoter can be included in the heterologous nucleic acid molecule. When more than one promoter is included in the heterologous nucleic acid molecule, each of the promoters is operatively linked to the nucleic acid sequence coding for the heterologous protein. The promoters can be located, in view of the nucleic acid molecule coding for the heterologous protein, upstream, downstream as well as both upstream and downstream.

"Promoter" refers to a DNA fragment capable of controlling the expression of a coding sequence or functional RNA. The term "expression," as used herein, refers to the transcription and stable accumulation of sense (mRNA) from the heterologous nucleic acid molecule described herein. Expression may also refer to translation of mRNA into a polypeptide. Promoters may be derived in their entirety from a native gene, or be composed of different elements derived from different promoters found in nature, or even comprise synthetic DNA segments. It is understood by those skilled in the art that different promoters may direct the expression at different stages of development, or in response to different environmental or physiological conditions. Promoters which cause a gene to be expressed in most cells at most times at a substantial similar level are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of the polymerase.

The promoter can be heterologous to the nucleic acid molecule encoding the heterologous protein. The promoter can be heterologous or derived from a strain being from the same genus or species as the recombinant yeast host cell. In an embodiment, the promoter is derived from the same genera or species of the yeast host cell and the heterologous protein is derived from different genera that the yeast host cell.

In the context of the present disclosure, the heterologous protein can be further modified to include a tethering region (so as to allow the localization of the secreted heterologous protein at the external surface of the yeast host cell) and/or fused to another entity (to create a fusion protein). Alternatively, the heterologous protein (such as the heterologous trehalase) can be modified so as to remove its tethering region.

In the context of the present disclosure, the recombinant yeast host cell can include at least two "second" genetic modifications, one in leading to the reduction in the production of one or more native enzymes that function to produce trehalose or regulating trehalose synthesis and another one leading to the expression of an heterologous trehalase.

In some instances, the recombinant yeast host cell can include a further genetic modification for reducing the production of one or more native enzyme that function to catabolize (breakdown) formate. As used in the context of the present disclosure, the expression "native polypeptides that function to catabolize formate" refers to polypeptides which are endogenously found in the recombinant yeast host cell. Native enzymes that function to catabolize formate include, but are not limited to, the FDH1 and the FDH2 polypeptides (also referred to as FDH1 and FDH2 respectively). In an embodiment, the recombinant yeast host cell bears a genetic modification in at least one of the fdh1 gene (encoding the FDH1 polypeptide), the fdh2 gene (encoding the FDH2 polypeptide) or orthologs thereof. In another embodiment, the recombinant yeast host cell bears genetic modifications in both the fdh1 gene (encoding the FDH1 polypeptide) and the fdh2 gene (encoding the FDH2 polypeptide) or orthologs thereof. Examples of recombinant yeast host cells bearing such genetic modification(s) leading to the reduction in the production of one or more native enzymes that function to catabolize formate are described in WO 2012/138942. Preferably, the recombinant yeast host cell has genetic modifications (such as a genetic deletion or insertion) in the fdh1 gene and in the fdh2 gene which would cause the host cell to have knocked-out fdh1 and fdh2 genes.

In some instances, the recombinant yeast host cell can include a further genetic modification allowing the expression of an heterologous glucoamylase. In an embodiment, the heterologous glucoamylase is derived from a γ-amylase, such as, for example, the glucoamylase of Saccharomycoces filbuligera (e.g., encoded by the glu 0111 gene). In instances in which the recombinant yeast host cell is intended to be used at elevated temperatures, genetic modifications for increasing the robustness of a genetically-modified recombinant yeast host cell expressing an heterologous glucoamylase are described in PCT/IB2016/055162 filed on Aug. 29, 2016 and herewith incorporated in its entirety.

The recombinant yeast host cell can be further genetically modified to allow for the production of additional heterologous proteins. In an embodiment, the recombinant yeast host cell can be used for the production of an enzyme, and especially an enzyme involved in the cleavage or hydrolysis of its substrate (e.g., a lytic enzyme and, in some embodiments, a saccharolytic enzyme). In still another embodiment, the enzyme can be a glycoside hydrolase. In the context of the present disclosure, the term "glycoside hydrolase" refers to an enzyme involved in carbohydrate digestion, metabolism and/or hydrolysis, including amylases, cellulases, hemicellulases, cellulolytic and amylolytic accessory enzymes, inulinases, levanases, trehalases, pectinases, and pentose sugar utilizing enzymes. In another embodiment, the enzyme can be a protease. In the context of the present disclosure, the term "protease" refers to an enzyme involved in protein digestion, metabolism and/or hydrolysis. In yet another embodiment, the enzyme can be an esterase. In the context of the present disclosure, the term "esterase" refers to an enzyme involved in the hydrolysis of an ester from an acid or an alcohol, including phosphatases such as phytases.

The additional heterologous protein can be an "amylolytic enzyme", an enzyme involved in amylase digestion, metabolism and/or hydrolysis. The term "amylase" refers to an enzyme that breaks starch down into sugar. All amylases are glycoside hydrolases and act on α-1,4-glycosidic bonds. Some amylases, such as γ-amylase (glucoamylase), also act on α-1,6-glycosidic bonds. Amylase enzymes include α-amylase (EC 3.2.1.1), γ-amylase (EC 3.2.1.2), and γ-amylase (EC 3.2.1.3). The α-amylases are calcium met alloenzymes, unable to function in the absence of calcium. By acting at random locations along the starch chain, α-amylase breaks down long-chain carbohydrates, ultimately yielding maltotriose and maltose from amylose, or maltose, glucose and "limit dextrin" from amylopectin. Because it can act anywhere on the substrate, α-amylase tends to be faster-acting than β-amylase. In an embodiment, the heterologous protein is derived from a α-amylase such as, for example, from the α-amylase of *Bacillus* amyloliquefacens. Another form of amylase, β-amylase is also synthesized by bacteria, fungi, and plants. Working from the non-reducing end, β-amylase catalyzes the hydrolysis of the second α-1,4 glycosidic bond, cleaving off two glucose units (maltose) at a time. Another amylolytic enzyme is α-glucosidase that acts on maltose and other short malto-oligosaccharides produced by α-, β-, and γ-amylases, converting them to glucose. Another amylolytic enzyme is pullulanase. Pullulanase is a specific kind of glucanase, an amylolytic exoenzyme, that degrades pullulan. Pullulan is regarded as a chain of maltotriose units linked by alpha-1,6-glycosidic bonds. Pullulanase (EC 3.2.1.41) is also known as pullulan-6-glucanohydrolase (debranching enzyme). Another amylolytic enzyme, isopullulanase, hydrolyses pullulan to isopanose (6-alpha-maltosylglucose). Isopullulanase (EC 3.2.1.57) is also known as pullulan 4-glucanohydrolase. An "amylase" can be any enzyme involved in amylase digestion, metabolism and/or hydrolysis, including α-amylase, β-amylase, glucoamylase, pullulanase, isopullulanase, and alpha-glucosidase.

The additional heterologous protein can be a "cellulolytic enzyme", an enzyme involved in cellulose digestion, metabolism and/or hydrolysis. The term "cellulase" refers to a class of enzymes that catalyze cellulolysis (i.e. the hydrolysis) of cellulose. Several different kinds of cellulases are known, which differ structurally and mechanistically. There are general types of cellulases based on the type of reaction catalyzed: endocellulase breaks internal bonds to disrupt the crystalline structure of cellulose and expose individual cellulose polysaccharide chains; exocellulase cleaves 2-4 units from the ends of the exposed chains produced by endocellulase, resulting in the tetrasaccharides or disaccharide such as cellobiose. There are two main types of exocellulases (or cellobiohydrolases, abbreviate CBH)—one type working processively from the reducing end, and one type working processively from the non-reducing end of cellulose; cellobiase or beta-glucosidase hydrolyses the exocellulase product into individual monosaccharides; oxidative cellulases that depolymerize cellulose by radical reactions, as for instance cellobiose dehydrogenase (acceptor); cellulose phosphorylases that depolymerize cellulose using phosphates instead of water. In the most familiar case of cellulase activity, the enzyme complex breaks down cellulose to beta-glucose. A "cellulase" can be any enzyme involved in cellulose digestion, metabolism and/or hydrolysis, including an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, and feruoyl esterase protein.

The additional heterologous protein can have "hemicellulolytic activity", an enzyme involved in hemicellulose digestion, metabolism and/or hydrolysis. The term "hemicellulase" refers to a class of enzymes that catalyze the hydrolysis of cellulose. Several different kinds of enzymes are known to have hemicellulolytic activity including, but not limited to, xylanases and mannanases.

The additional heterologous protein can have "xylanolytic activity", an enzyme having the is ability to hydrolyze glycosidic linkages in oligopentoses and polypentoses. The term "xylanase" is the name given to a class of enzymes which degrade the linear polysaccharide beta-1,4-xylan into xylose, thus breaking down hemicellulose, one of the major components of plant cell walls. Xylanases include those enzymes that correspond to Enzyme Commission Number 3.2.1.8. The heterologous protein can also be a "xylose metabolizing enzyme", an enzyme involved in xylose digestion, metabolism and/or hydrolysis, including a xylose isomerase, xylulokinase, xylose reductase, xylose dehydrogenase, xylitol dehydrogenase, xylonate dehydratase, xylose transketolase, and a xylose transaldolase protein. A "pentose sugar utilizing enzyme" can be any enzyme involved in pentose sugar digestion, metabolism and/or hydrolysis, including xylanase, arabinase, arabinoxylanase, arabinosidase, arabinofuranosidase, arabinoxylanase, arabinosidase, and arabinofuranosidase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and/or xylose transaldolase.

The additional heterologous protein can have "mannanic activity", an enzyme having the is ability to hydrolyze the terminal, non-reducing β-D-mannose residues in β-D-mannosides. Mannanases are capable of breaking down hemicellulose, one of the major components of plant cell walls. Xylanases include those enzymes that correspond to Enzyme Commission Number 3.2.25.

The additional heterologous protein can be a "pectinase", an enzyme, such as pectolyase, pectozyme and polygalacturonase, commonly referred to in brewing as pectic enzymes. These enzymes break down pectin, a polysaccharide substrate that is found in the cell walls of plants.

The additional heterologous protein can have "phytolytic activity", an enzyme catalyzing the conversion of phytic acid into inorganic phosphorus. Phytases (EC 3.2.3) can be belong to the histidine acid phosphatases, β-propeller phytases, purple acid phosphastases or protein tyrosine phosphatase-like phytases family.

The additional heterologous protein can have "proteolytic activity", an enzyme involved in protein digestion, metabolism and/or hydrolysis, including serine proteases, threonine proteases, cysteine proteases, aspartate proteases, glutamic acid proteases and met alloproteases.

When the recombinant yeast host cell expresses an heterologous protein, it can be further modified to increase its robustness at high temperatures. Genetic modifications for increasing the robustness of a genetically-modified recombinant yeast host cell are described in U.S. 62/214,412 filed on Sep. 4, 2015 and herewith incorporated in its entirety.

Methods of Using the Recombinant Yeast Host Cells for Limiting the Accumulation of Trehalose During Fermentation The recombinant yeast host cells described herein can be used to limit and, in some embodiments, prevent the production, accumulation or excretion of trehalose during fermentation. As indicated above, the recombinant yeast host cells have a second genetic modification which either limits the production of endogenous trehalose by the recombinant yeast or hydrolyzes the trehalose that is being endogenously production. The process comprises combining a substrate to be hydrolyzed (optionally included in a fermentation medium) with the recombinant yeast host cells. In an embodiment, the substrate to be hydrolyzed is a lignocellulosic biomass and, in some embodiments, it comprises starch (in a gelatinized or raw form). In other embodiments, the substrate to be hydrolyzed comprises maltodextrin. In some embodiments, the use of recombinant yeast host cells limits or avoids the need of adding trehalase in a purified form during fermentation to limit the amount of trehalose. This embodiment is advantageous because it can reduce or eliminate the need to supplement the fermentation medium with external source of purified enzymes (e.g., glucoamylase and/or trehalase) while allowing the fermentation of the lignocellulosic biomass into a fermentation product (such as ethanol). However, in some circumstances, it may be advisable to supplement the medium with a trehalase (such as, for example, the trehalase having the amino acid sequence of SEQ ID NO: 1 or 2) in a purified. Such trehalase can be produced in a recombinant fashion in a recombinant yeast host cell.

The recombinant yeast host cells described herein can be used to increase the production of a fermentation product during fermentation. As indicated above, the recombinant yeast host cells have a second genetic modification which either limits the production of endogenous trehalose by the recombinant yeast or hydrolyzes the trehalose that is being endogenously production and such second genetic modifications can improve the yield in one or more fermentation products. The process comprises combining a substrate to be hydrolyzed (optionally included in a fermentation medium) with the recombinant yeast host cells. In an embodiment, the substrate to be hydrolyzed is a lignocellulosic biomass and, in some embodiments, it comprises starch (in a gelatinized or raw form). In some embodiments, the use of recombinant yeast host cells limits or avoids the need of adding trehalase in a purified form during fermentation to limit the amount of trehalose. This embodiment is advantageous because it can reduce or eliminate the need to supplement the fermentation medium with external source of purified enzymes (e.g., glucoamylase and/or trehalase) while allowing the fermentation of the lignocellulosic biomass into a fermentation product (such as ethanol). However, in some circumstances, it may be advisable to supplement the medium with a trehalase (such as, for example, the trehalase having the amino acid sequence of SEQ ID NO: 1 or 2) in a purified. Such trehalase can be produced in a recombinant fashion in a recombinant yeast host cell.

The production of ethanol can be performed at temperatures of at least about 25° C., about 28° C., about 30° C., about 31° C., about 32° C., about 33° C., about 34° C., about 35° C., about 36° C., about 37° C., about 38° C., about 39° C., about 40° C., about 41° C., about 42° C., or about 50° C. In some embodiments, when a thermotolerant yeast cell is used in the process, the process can be conducted at temperatures above about 30° C., about 31° C., about 32° C., about 33° C., about 34° C., about 35° C., about 36° C., about 37° C., about 38° C., about 39° C., about 40° C., about 41° C., about 42° C., or about 50° C.

In some embodiments, the process can be used to produce ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter.

Ethanol production can be measured using any method known in the art. For example, the quantity of ethanol in fermentation samples can be assessed using HPLC analysis. Many ethanol assay kits are commercially available that use, for example, alcohol oxidase enzyme based assays.

The present invention will be more readily understood by referring to the following examples which are given to illustrate the invention rather than to limit its scope.

Example I—Material and Methods

Strain M4652 was constructed using the KT (Kanamycin and HSV-thymidine kinase) and NT (nourseothricin and HSV-thymidine kinase) recyclable MX cassettes (FIG. 8A) targeting a direct integration and removal of the tps1 open reading frame. The KT-max and NT-max cassettes were PCR amplified, along with non-coding 5' and 3' flanks, creating overlapping homologous ends to promote recombination in vivo. The PCR products were transformed into the diploid *Saccharomyces cerevisiae* host strain, M2390, and subsequently selected on YPD containing G418 (200 µg/ml) and cloNat (100 µg/ml) to select for removal of both tps1 alleles. Table 1 below provides the nucleic acid sequence of the primers used to make the MA613 genetic cassette used to create the M4652 strain.

TABLE 1

Nucleic acid sequence of the primers used to make the MA613 genetic cassette used to create the M4652 strain.

| Target | SEQ ID NO: | Sequence |
|---|---|---|
| TPS1 5' Flank | 19 | GCAGAGGATTACTT GGACATTAACGGTT CTCCTATC |
|  | 20 | GGACGAGGCAAGCTA AACAGATCTCTAGAC CTAAGTTCTATGTCT TAATAAGTCTGTATG |

TABLE 1-continued

Nucleic acid sequence of the primers used to make the MA613 genetic cassette used to create the M4652 strain.

| Target | SEQ ID NO: | Sequence |
|---|---|---|
| KT-MX and NT-MX | 21 | TACTCACATACAGAC TTATTAAGACATAGA ACTTAGGTCTAGAGA TCTGTTTAGCTTGCC |
|  | 22 | GAATAGACGATCGTC TCATTTGCATCGGGT TCAGAGACTACATGA TAGTCCAAAGAAAAG |
| TPS2 3' Flank | 23 | CCGTTTCTTTTCTTT GGACTATCATGTAGT CTCTGAACCCGATGC AAATGAGACGATCGT |
|  | 24 | GCAAGAGGCTCCTCC ACTGGCATTTTCACG ATTTGG |

Strain M4653 was constructed using the same method as described in the M4652 engineering. However, the 5' and 3' non-coding flanking regions were designed to target the tps2 region (FIG. 8B) for the deletion of the tps2 open reading frame. Table 2 below provides the nucleic acid sequence of the primers used to make the MA614 genetic cassette used to create the M4653 strain.

TABLE 2

Nucleic acid sequence of the primers used to make the MA614 genetic cassette used to create the M4653 strain.

| Target | SEQ ID NO: | Sequence |
|---|---|---|
| TPS2 5' Flank | 25 | GCTGTGCAGCAG GGTATTCTACTA CGTGTTAGCTT |
|  | 26 | GGACGAGGCAAG CTAAACAGATCT CTAGACCTATTC GGCACAGAAATA GTGACAGGCAGT |
| KT-MX and NT-MX | 27 | AATAACACTGCC TGTCACTATTTC TGTGCCGAATAG GTCTAGAGATCT GTTTAGCTTGCC |
|  | 28 | TCTAGTCATAAC CATTTCGTTAAA AAGGGTGTTGAG ACTACATGATAG TCCAAAGAAAAG |
| TPS2 3' Flank | 29 | CCGTTTCTTTTC TTTGGACTATCA TGTAGTCTCAAC ACCCTTTTTAAC GAAATGGTTATG |
|  | 30 | CGTAGATCGACC TTGCCTGGAATC CCAGGTT |

Figure 8A:
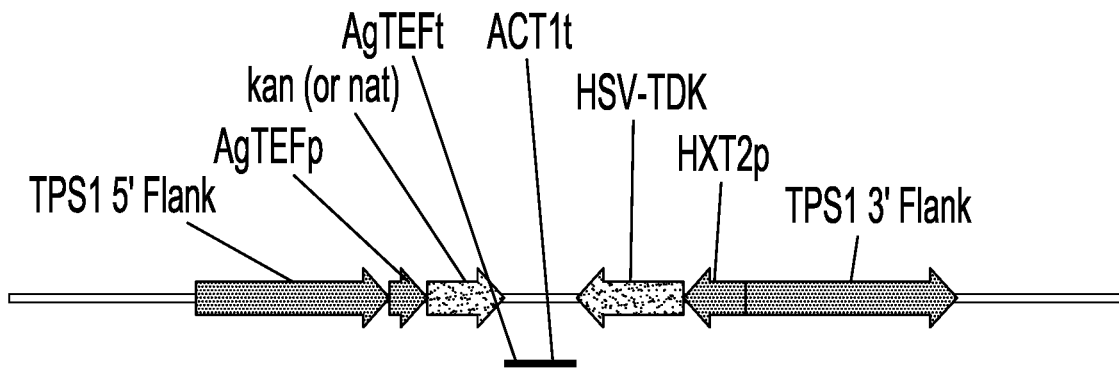
Figure 8B:
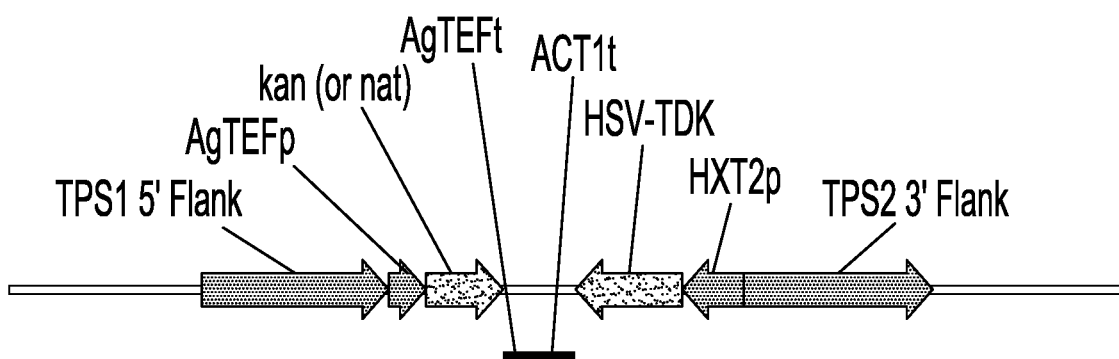
Figure 8C:
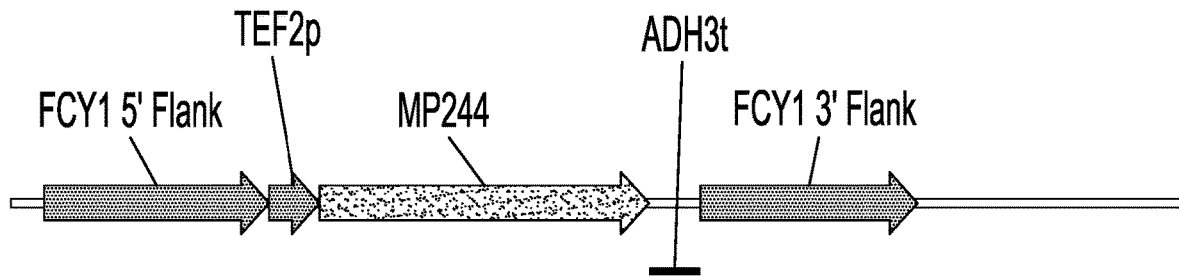

Strain M11245 was engineered to express an heterologous trehalase. The heterologous trehalase gene, MP244 (SEQ ID NO: 1) was codon-optimized for *S. cerevisiae* based on the amino acid sequence from *Aspergillus fumigatus* (GenBank Accession No. XP_748551). The synthesized sequence was used as PCR template to create homologous ends with the *S. cerevisiae* tef2 promoter and adh3 terminator and integrated at the FCY1 loci in the diploid *S. cerevisiae* host strain via homologous recombination in vivo (FIG. 8C). Table 3 below provides the nucleic acid sequence of the primers used to make the MA1920 genetic cassette used to create the M11245 strain.

TABLE 3

Nucleic acid sequence of the primers used to make the MA1920 genetic cassette used to create the M11245 strain.

| Target | SEQ ID NO: | Sequence |
|---|---|---|
| FCY1 5' Flank | 31 | CTCGTTGGTAGG GTCCACACCATA GACTTCAG |
|  | 32 | TAGCTATGAAAT TTTTAACTCTTT AAGCTGGCTCT |
| TEF2p | 33 | GATGAGAGCCAG CTTAAAGAGTTA AAAATTTCATAG CTAGGGCGCCAT AACCAAGGTATC |
|  | 34 | CCAACAAAGAAA CCCAAGTAGCCA AGTTTTGAGACA ACATGTTTAGTT AATTATAGTTCG |
| MP244 | 35 | GAATATACGGTC AACGAACTATAA TTAACTAAACAT GTTGTCTCAAAA CTTGGC |
|  | 36 | CAAAGACTTTCA TAAAAAGTTTGG GTGCGTAACACG CTATCAAGCGTT GAATTGTCTG |
| ADH3t | 37 | GCTTTGAACGAC AGAAGATACAGA CAATTCAACGCT TGATAGCGTGTT ACGCACCCAAAC |
|  | 38 | TATATAAAATTA AATACGTAAATA CAGCGTGCTGCG TGCTATGAGGAA GAAATCCAAATC |
| FCY1 3' Flank | 39 | AGCACGCAGCAC GCTGTATTTACG TATTTAATTTT |
|  | 40 | GTAGTGCTGTCT GAACAGAATAAA TGCGTTCTTGG |

Figure 8D:
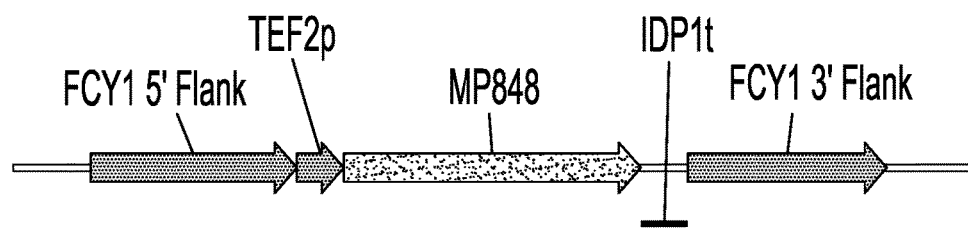
Figure 8E:
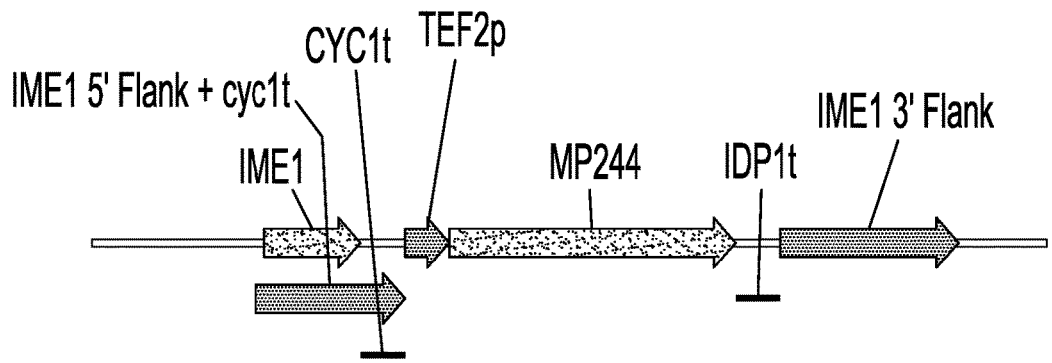

Strain M10957 was engineered to express an heterologous trehalase. The heterologous trehalase gene, MP848 (SEQ ID NO: 2) was codon-optimized for *S. cerevisiae* based on the amino acid sequence from *Aspergillus nidulans* (GenBank Accession No. P78617). The synthesized sequence was used as PCR template to create homologous ends with the *S. cerevisiae* tef2 promoter and adh3 terminator and integrated at the FCY1 loci in the diploid *S. cerevisiae* host strain via homologous recombination in vivo (FIG. 8D). Table 4 below provides the nucleic acid sequence of the primers used to make the MAP516 genetic cassette used to create the M10957 strain.

TABLE 4

Nucleic acid sequence of the primers used to make the MAP516 genetic cassette used to create the M10957 strain.

| Target | SEQ ID NO: | Sequence |
|---|---|---|
| FCY1 5' Flank | 41 | CTGACTCGTTGGTGGGGTCCACACCATAGA |
|  | 42 | GATTGGCGGTCTATAGATACCTTGGTTATGGCGCCCTAGCTATGAAATTTTTAACTCTTC |
| TEF2p | 43 | GAGAGCCAGCTTTTTGAAGAGTTAAAAATTTCATAGCTAGGGCGCCATAACCAAGGTATC |
|  | 44 | GTTTAGTTAATTATAGTTCG |
| MP848 | 45 | TTTTTAGAATATACGGTCAACGAACTATAATTAACTAAACATGAGATTCAAGTCCGTTTT |
|  | 46 | AATGAAAAAAAAGTGGTAGATTGGGCTACGTAAATTCGATTACAACAAAGGAACTGGTT |
| ADH3t | 47 | TCGAATTTACGTAGCCCAATC |
|  | 48 | TATATAAAATTAAATACGTAAATACAGCGTGCTGCGTGCTCAAATGACGTCAAAGAAGT |
| FCY1 3' Flank | 49 | CATAGGCTCATATAATACTTCTTTTGACGTCATTTGAGCACGCAGCACGCTGTATTTACG |
|  | 50 | GTAGTGCTGTCTGAACAGAATAAATGCGTTCT |

Strain M12121 was constructed using the M11589 background containing the glycerol reduction pathway and heterologous glu011-CO glucoamylase The synthesized sequence was used as PCR template to create homologous ends with the *S. cerevisiae* tef2 promoter and adh3 terminator and integrated at the IME loci in the diploid *S. cerevisiae* host strain via homologous recombination in vivo (FIG. 80). Table 5 below provides the nucleic acid sequence of the primers used to make the MAP811 genetic cassette used to create the M12121 strain.

TABLE 5

Nucleic acid sequence of the primers used to make the MAP811 genetic cassette used to create the M12121 strain.

| Target | SEQ ID NO: | Sequence |
|---|---|---|
| IME1 5' Flank | 51 | CACCTACAGAGAAACAAATTCCTACTGGCACCC |
|  | 52 | TTGGCGGTCTATAGATACCTTGGTTATGCGCCCGTCGACAACTAAACTGGAATGTGAGG |
| TEF2p | 53 | ACTTTTGTTGTTCCCTCACATTCCAGTTTAGTTGTCGACGGGCGCCATAACCAAGGTATC |
|  | 54 | CCAACAAAGAAACCAAGTAGCCAAGTTTTGAGACAACATGTTTAGTTAATTATAGTTCG |
| MP244 | 55 | GAATATACGGTCAACGAACTATAATTAACTAAACATGTTGTCTCAAAACTTGGCTACTTG |
|  | 56 | AAATGAAAAAAAAGTGGTAGATTGGGCTACGTAAATTCGATCAAGCGTTGAATTGTCTG |
| IDP1t | 57 | GCTTTGAACGACAGAAGATACAGACAATTCAACGCTTGATCGAATTTACGTAGCCCAATC |
|  | 58 | ATTTTGAGGGAAGGGGGAAGATTGTAGTACTTTTCGAGAACAAATGACGTCAAAAGAAGT |
| IME1 3' Flank | 59 | TAGGCTCATATAATACTTCTTTTGACGTCATTTGTTCTCGAAAAGTACTACAATCTTCCC |
|  | 60 | GAACTTCTGCCTTTGAACAATTTCCAAACAATTTTCATTGGTC |

Table 6 summarizes the strains used in the Examples.

TABLE 6

Description of the *S. cerevisiae* strains used in the examples.

| Name | Gene inactivated | Gene overexpressed |
|---|---|---|
| M2390 (wild-type) | None | None |
| M4652 | Δtps1 | None |
| M4653 | Δtps2 | None |
| M11245 | None | Gene encoding GeneBank Accession XP_748551 (MP244) |
| M10957 | None | Gene encoding GeneBank Accession P78617 (MP848) |

TABLE 6-continued

Description of the *S. cerevisiae* strains used in the examples.

| Name | Gene inactivated | Gene overexpressed |
| --- | --- | --- |
| M8841 (described in WO2011/153516 and WO2012/138942) | Δgpd2 Δfdh1 Δfdh2 Δfcy1 | Gene encoding *Saccharomycopsis fibuligera* glu0111 (GeneBank Accession CAC83969.1) Gene encoding the PFLA polypeptide (UnitProtKB Accession A1A239) Gene encoding the PFLB polypeptide (UnitProtKB Accession A1A240) Gene encoding the ADHE polypeptide (UnitProtKB Accession A1A067) |
| M11589 | Δgpd2 Δfdh1 Δfdh2 Δfcy1 | *Saccharomycopsis fibuligera* glu0111 (GeneBank Accession CAC83969.1) Gene encoding the PFLA polypeptide (UnitProtKB Accession A1A239) Gene encoding the PFLB polypeptide (UnitProtKB Accession A1A240) Gene encoding the ADHE polypeptide (UnitProtKB Accession A1A067) Gene encoding *Saccharomyces cerevisiae* STL1 (GeneBank Accession NP_010825) |
| M12121 | Δgpd2 Δfdh1 Δfdh2 Δfcy1 | Gene encoding GeneBank Accession XP_748551 (MP244) Gene encoding *Saccharomycopsis fibuligera* glu0111 (GeneBank Accession CAC83969.1) Gene encoding the PFLA polypeptide (UnitProtKB Accession A1A239) Gene encoding the PFLB polypeptide (UnitProtKBAccession A1A240) Gene encoding the ADHE polypeptide (UnitProtKB Accession A1A067) Gene encoding *Saccharomyces cerevisiae* STL1 (GeneBank Accession NP_010825) |
| M13913 | Δgpd2 Δfdh1 Δfdh2 Δfcy1 | Gene encoding GeneBank Accession XP_748551 (MP244) Gene encoding *Saccharomycopsis fibuligera* glu0111 (GeneBank Accession CAC83969.1) Gene encoding the PFLA polypeptide (UniProtKB Accession A1A239) Gene encoding the PFLB polypeptide (UniProtKB Accession A1A240) Gene encoding the ADHE polypeptide (UniProtKB Accession A1A067) |

Fermentation using solid corn mash. Conditions for the results presented in FIG. 2: the fermentation was performed using 20% total solids (Ts) liquefied corn mash with the addition of 1000 ppm urea, 0.6 amyloglucosidase unit (AGU)/grams of total solids (gTs) commercial glucoamylase enzyme, 0.1 g/L dry cell weight (DCW) inoculum, with a total fermentation time of 51 h. Temperatures were held at 35° C. for 24 h and lowered to 32° C. for the remainder of the fermentation. Samples were collected and analyzed on HPLC for ethanol titers. Conditions for the results presented in FIG. 5: the fermentation was performed using 25.5% Ts liquefied corn mash with the addition of 500 ppm urea, 0.6 AGU/gTs, commercial glucoamylase for M2390, 0.3 AGU/gTs GA for M8841, and 100 µg/ml of purified MP244, 0.3 g/L dry cell weight (DCW) inoculum, with a total fermentation time of 53 h. Temperatures were held at 35° C. for 24 h and lowered to 32° C. for the remainder of the fermentation. Samples were collected and analyzed on HPLC for ethanol titers and residual trehalose. Conditions for the results presented in FIG. 7: the fermentation was performed using 32% Ts with the addition of 700 ppm urea, 0.48 AGU/gTs commercial glucoamylase for M2390, 0.24 AGU/gTs GA for M11589 and M12121, 0.3 g/L dry cell weight (DCW) inoculum, with a total fermentation time of 48 h. The temperature was held at 33° C. for 24 h and lowered to 31° C. for the remainder of the fermentation. Samples were collected and analyzed on HPLC for ethanol titers and residual trehalose.

Extracellular trehalose assay. Residual trehalose was measure using HPLC.

Extracellular trehalase assay. For evaluation of strains expressing secreted heterologous trehalases, a plate based trehalase assay was performed. Strains of interest were 24-72 h in YPD. The cultures were then centrifuged at 3000 rpm to separate the cells from the culture supernatant containing the secreted enzymes. The supernatant is then added to a 1% trehalose solution in 50 mM sodium acetate buffer (pH 5.0). The assay is conducted using a 5:1 trehalose solution:supernatant ratio and incubated at 35° C. for 2 h. The reducing sugars were measured using the dinitrosalicylic acid reagent solution (DNS) method, using a 2:1 DNS:starch assay ratio and boiled at 100° C. for 5 mins. The absorbance is measured at 540 nm.

Intracellular trehalose assay. For evaluation of intracellular trehalose concentrations, strains were grown in YPD at 35° C. Cells were centrifuged at 3000 rpm and the supernatant removed, followed by a repeated water wash. Cultures were normalized to the same OD and 0.25 M sodium carbonate added and incubated at 95° C. for 2 h. Next, 0.2 M sodium acetate pH 5.2 was added, followed by the addition of 1 M acetic acid. A total of 0.5 ml of the slurry was treated with 10 µl of of Megazyme E-trehalase and incubated overnight at 37° C. Glucose was measured using HPLC.

Fermentation using maltodextrin. The fermentation was performed using 260 g/L maltodextrin with the addition of 10 g/L yeast extract, 1 g/L citrate, 500 ppm urea, 0.6 amyloglucosidase unit (AGU)/grams of total solids (gTs) commercial glucoamylase enzyme for the wild type M2390, and 0.3 AGU/gTs for the M8841 and M13913 strains, 0.1 g/L dry cell weight (DCW) inoculum, with a total fermentation time of 54 h. Temperatures were held at 35° C. for 24 h and lowered to 32° C. for the remainder of the fermentation. Samples were collected and analyzed on HPLC for ethanol titers and residual trehalose.

Example II—Elimination of Key Biosynthetic Genes for the PRODUCTION OF TREHALOSE The material, methods and strains used in this example were presented in Example I.

Figure 1:
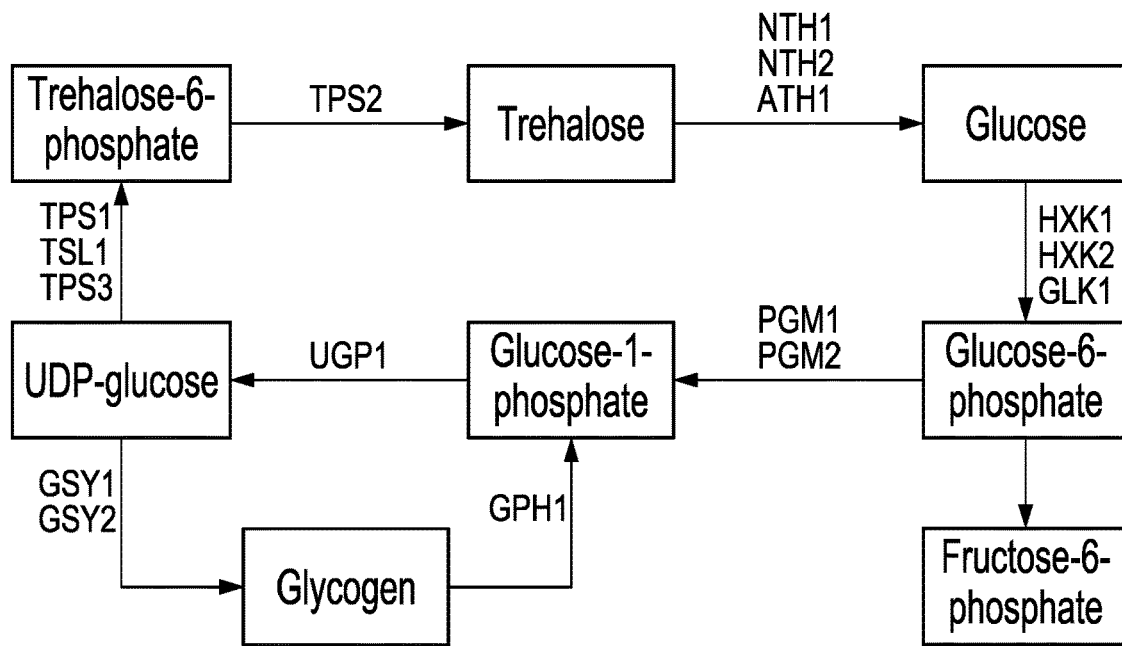
FIG. 1 illustrates the trehalose synthesis pathway. Abbreviations: HXK=hexokinase; GLK=glucokinase; PGM=phosphoglucomutase; UGP1=UDP-glucose pyrophosphorylase; GSY=glycogen synthase; GPH=Glycogen phosphorylase; TPS1=trehalose-6-phosphate synthase; TPS3=trehalose-6-phosphate synthase; TSL1=trehalose synthase long chain; TPS2=trehalose-6-phosphate phosphatase; NTH=neutral trehalase; ATH1=acid trehalase.
Figure 2:
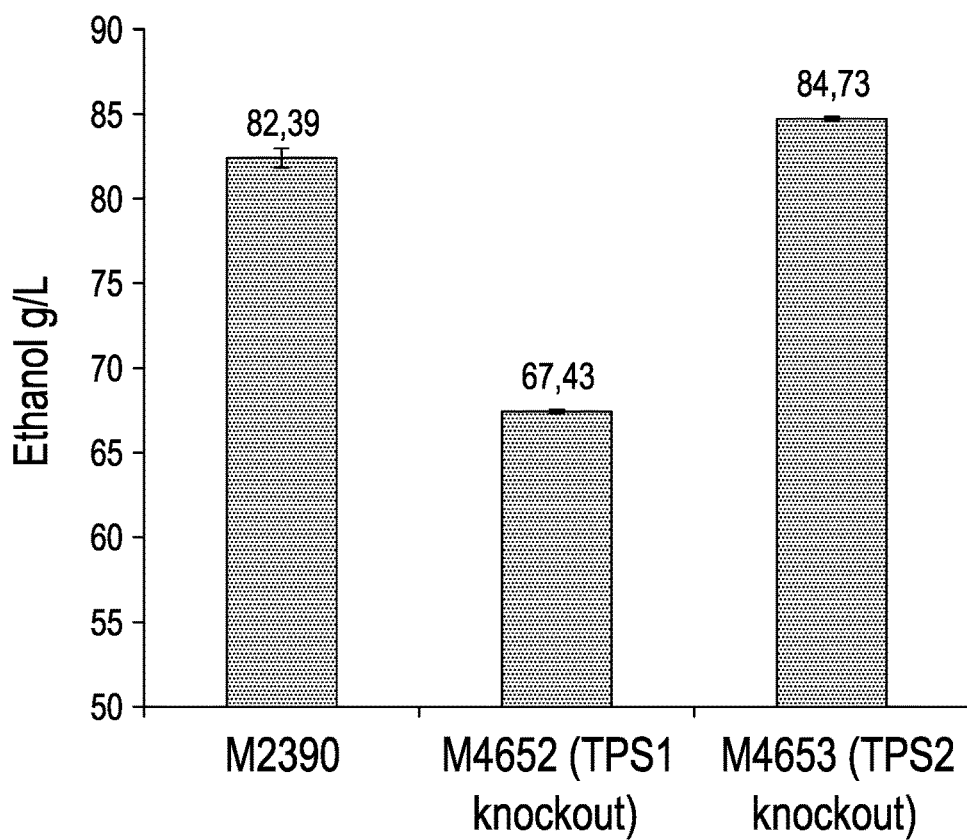
FIG. 2 illustrates the effect of TPS1 (M4652) and TPS2 (M4653) knockouts on ethanol production in 20% corn mash fermentation compared to the conventional parent strain (M2390). Results are shown as ethanol concentration (in g/L) in function of strains used.
Figure 3:
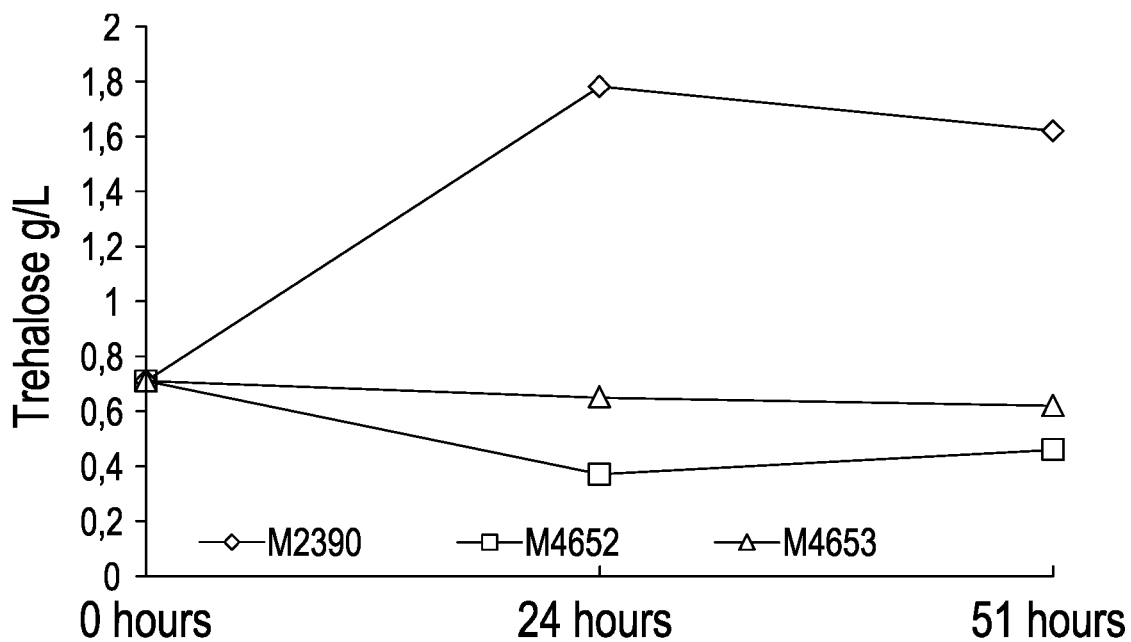
FIG. 3 illustrates the effect of TPS1 (M4652 or ■) and TPS2 (M4653 or ▲) knockouts on trehalose production in 20% corn mash fermentation compared to the conventional parent strain (M2390 or ♦). Results are shown as trehalose concentration (in g/L) in function of strains used.

In order to down regulate/eliminate trehalose production, the native genes responsible for the primary synthetic functions (tps1 and tps2) were individually knocked out in the conventional (wild-type) strain M2390. The M4652 and M4653 strains were then evaluated in corn mash fermentation to characterize ethanol production and residual trehalose. As shown in FIG. 2, the Δtps2 strain (M4653) performed well, providing an additional 2.2 g/L of ethanol production over the conventional strain (M2390), coupled with an 86% reduction in residual trehalose (FIG. 3).

Example III—Expression and Secretion of Heterologous TREHALASES TARGETING HYDROLYSIS OF RESIDUAL TREHALOSE The material, methods and strains used in this example were presented in Example I.

In order to target the hydrolysis of residual trehalose in an ethanol fermentation, various heterologous trehalases were cloned by integrating 2 copies of the sequence into the conventional yeast host background (M2390) and expressed in *S. cerevisiae*. The screened heterologous trehalase sequences are presented in Table 7.

TABLE 7

Figure 4:
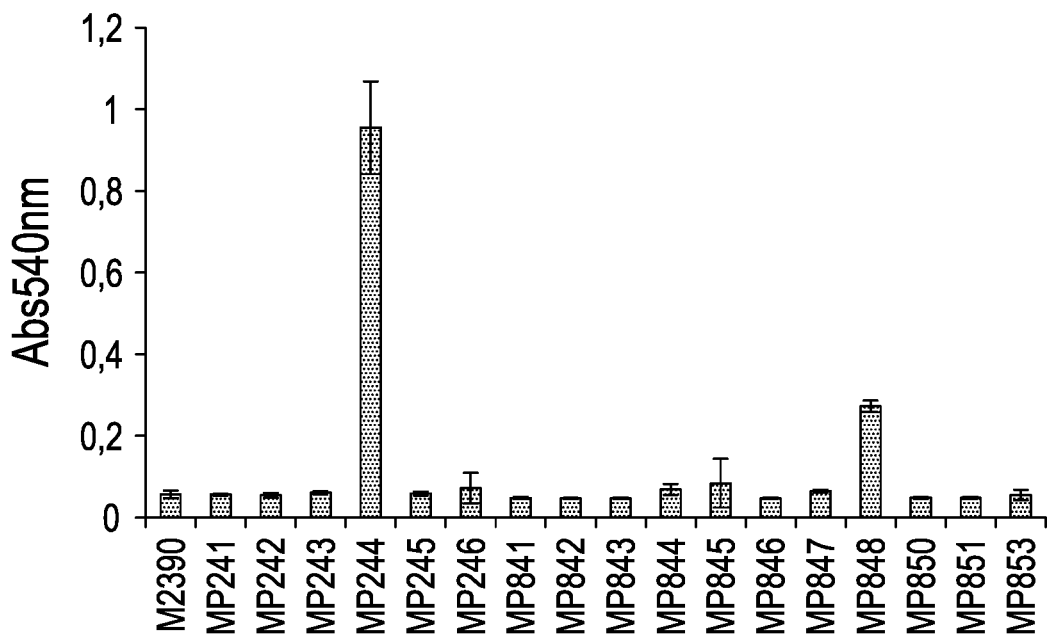
FIG. 4 illustrates the results of a secreted trehalase assay of strains expressing various heterologous trehalases. The results are provided as absorbance at 450 nm in function of strain used. The parental strain M2390 was used as a control. Results are shown were for the following heterologous trehalase MP241 (SEQ ID NO: 4), MP242 (SEQ ID NO: 5), MP243 (SEQ ID NO: 6), MP244 (SEQ ID NO: 1), MP245 (SEQ ID NO: 7), MP246 (SEQ ID NO: 8), MP841 (SEQ ID NO: 9), MP842 (SEQ ID NO: 10), MP843 (SEQ ID NO: 11), MP844 (SEQ ID NO: 12), MP845 (SEQ ID NO: 13), MP846 (SEQ ID NO: 14), MP847 (SEQ ID: 15), MP848 (SEQ ID NO: 2), MP850 (SEQ ID NO: 16), MP851 (SEQ ID NO: 17) and MP853 (SEQ ID NO: 18). MP244 and MP848 were identified as the most active when compared to the parental (negative control) strain M2390.

Amino acid sequence of the heterologous trehalase presented in FIG. 4.

| | Source | Accession # | SEQ ID NO: |
|---|---|---|---|
| MP241 | *Bacillusamyloliquefaciens* | CCG51384 | 4 |
| MP242 | *Debaryomyces hansenii* | CAG87277 | 5 |
| MP243 | *Aspergillus niger* | CAK43526 | 6 |
| MP244 | *Aspergillus fumigatus* | XP_748551 | 1 |
| MP245 | *Trichoderma reesei* | EGR45658 | 7 |
| MP246 | *Kluyveromyceslactis* | CAG99334 | 8 |
| MP841 | *Schizosaccharomyces pombe* | NP_595086 | 9 |
| MP842 | *Neurospora crassa* | XP_960845.1 | 10 |
| MP843 | *Candida albicans* | CAA64476.1 | 11 |
| MP844 | *Debaryomyces hansenii* | XP_459109 | 12 |
| MP845 | *Candida glabrata* | AGG12634 | 13 |
| MP846 | *Kluyveromyces lactis* | P49381 | 14 |
| MP847 | *Rasamsonia emersonii* | AAQ67343 | 15 |
| MP848 | *Aspergillus nidulans* | P78617 | 2 |
| MP850 | *Ashbya gossypii* | NP_984861 | 16 |
| MP851 | *Magnaporthe oryzae* | XP_003714173 | 17 |
| MP853 | *Thermus thermophilus* | YP_004082 | 18 |

The strains were then screened for secreted trehalase activity using a secreted trehalase assay. Results of the secreted trehalase assay are shown in FIG. 4. The MP244 (from *Aspergillus fumigatus*, Accession Number XP_748551 also shown as SEQ ID NO: 1) and MP848 (from *Aspergillus nidulans*, Accession Number P78617 also shown as SEQ ID NO: 2) trehalases exhibited increased trehalase activity.

The secreted protein MP244 was His-tagged and purified by FPLC to provide concentrated volumes of yeast-made isolated enzyme. A fermentation was performed using the M8841 strain, in the presence or the absence of 100 μg/mL of purified MP244 The results of such fermentation are shown in FIG. 5. The performance was also compared to the conventional strain (M2390). The addition of the MP244 trehalase provided a 1.25% yield increase over the M8841 strain with no trehalase added. The addition of the MP244 trehalase to the M8841 strain provided a total 3.65% yield increase over the conventional strain M2390. This was correlated with the reduction of residual trehalose measured at the end of fermentation (FIG. 6).

Example IV—Expression of Heterologous Trehalase and GLUCOAMYLASE TARGETING ETHANOL PRODUCTION The material, methods and strains used in this example were presented in Example I.

The heterologous trehalase gene, MP244 (SEQ ID NO: 1) was integrated into the genome of M11589, a strain expressing and secreting the heterologous glu011 glucoamylase from *S. fibuligera* and also possessing the glycerol reduction pathway The resulting strain, M12121 was subjected to a corn mash fermentation and compared to the parent M11589 along with a wild-type strain with no genetic modifications, M2390. As was observed with the exogenous addition of a trehalose, the expression of the MP244 trehalase provided an additional 1.1% yield increase (FIG. 7A) along with a measurable decrease in residual trehalose (FIG. 7B).

Example V—Maltodextrin Fermentation

Some of the material, methods and strains used in this example were presented in Example I.

The heterologous trehalase gene, MP244 (SEQ ID NO: 1) was integrated into the genome of M8841, a strain expressing and secreting the heterologous glu011 glucoamylase from *S. fibuligera* and also possessing the glycerol reduction pathway as described in WO 2012/138942. The resulting strain, M13913 was subjected to a 260 g/L maltodextrin fermentation and compared to the parent M8841 along with a wild-type strain with no genetic modifications, M2390. As was observed with the exogenous addition of a trehalose, the expression of the MP244 trehalase provided an additional 1.42% yield increase over the parent strain, M8841, and a total 3.1% yield increase over the wild type strain (FIG. 9A) along with a measurable decrease in residual trehalose (FIG. 9B). While the invention has been described in connection with specific embodiments thereof, it will be understood that the scope of the claims should not be limited by the preferred embodiments set forth in the examples, but should be given the broadest interpretation consistent with the description as a whole.

REFERENCES

WO 2011/153516

WO 2012/138942

An M Z, Tang Y Q, Mitsumasu K, Liu Z S, Shigeru M, Kenji K. Enhanced thermotolerance for ethanol fermentation of *Saccharomyces cerevisiae* strain by overexpression of the gene coding for trehalose-6-phosphate synthase. Biotechnol Lett. 33.7 (2011): 1367-1374.

Bell W., Sun W., Hohmann S., Wera S., Reinders A., De Virgilio C., Wiemken A., Thevelein J M. Composition and Functional Analysis of the *Saccharomyces cerevisiae* Trehalose Synthase Complex. Journal of Bio Chem. 11 (1998): 33311-33319.

Cao T S, Chi Z., Liu G L., Chi Z M. Expression of TPS1 gene from *Saccharomycopsis fibuligera* A11 in *Saccharomyces* sp. W0 enhances trehalose accumulation, ethanol tolerance, and ethanol production. Mol Biotechnol 56.1 (2014): 72-78.

Elbein A D, Pan Y T, Pastuszak I, Carroll D. New insights on trehalose: a multifunctional molecule. Glycobiology. 13.4 (2003): 17-27.

Ge X Y, Xu Y, Chen X. Improve carbon metabolic flux in *Saccharomyces cerevisiae* at high temperature by overexpressed TSL1 gene. J Ind Microbiol Biotechnol. 40 (2013): 345-352.

Giffen N. New Insights into fermentation drop samples: The real story of residual sugars. Fuel Ethanol Workshop and Expo. Minneapolis, M N. Jun. 5, 2012.

Guo Z P, Zhang L, Ding Z Y, Shi G Y. Minimization of glycerol synthesis in industrial ethanol yeast without influencing its fermentation performance. Metabol Eng 13.1 (2011): 49-59.

Singer M A and Lindquist S. Thermotolerance in *Saccharomyces cerevisiae*: the Yin and Yang of trehalose. Trends Biotechnol. 16.11 (1998): 460-468.

Thevelain J M. and Hohmann S. Trehalose synthase: guard to the gate of glycolysis in yeast? Trends Biochem Sci 20.1 (1995): 3-10.

What is claimed is:

1. A method of increasing the production of a fermentation product during a fermentation, said method comprising contacting a medium with (i) a recombinant yeast host cell comprising a first genetic modification for expressing a heterologous glucose-inactivated glycerol proton symporter STL1 (STL1) protein and (ii) a trehalase, wherein the production of the fermentation product is increased when compared to a control method with a control yeast host cell lacking the first genetic modification.

2. The method of claim 1, wherein the recombinant yeast host cell comprises a further genetic modification for reducing the production of one or more native enzymes that function to produce glycerol.

3. The method of claim 2, wherein the recombinant yeast host cell expresses less of a native glycerol-3-phosphate dehydrogenase 1 (GPD1) polypeptide than a control yeast host cell lacking the further genetic modification.

4. The method of claim 2, wherein the recombinant yeast host cell lacks the ability to produce a native GPD1 polypeptide.

5. The method of claim 2, wherein the recombinant yeast host cell expresses less of a native glycerol-3-phosphate dehydrogenase 2 (GPD2) polypeptide than a control yeast host cell lacking the further genetic modification.

6. The method of claim 2, wherein the recombinant yeast host cell lacks the ability to produce a native GPD2 polypeptide.

7. The method of claim 1, wherein the recombinant yeast host cell is from the genus *Saccharomyces* sp.

8. The method of claim 7, wherein the recombinant yeast host cell is from the species *Saccharomyces cerevisiae*.

9. The method of claim 1, wherein the trehalase is extracellular from the recombinant yeast host cell.

10. The method of claim 1, wherein the trehalase is provided in a purified form.

11. The method of claim 1, wherein the trehalase belongs to E.C. 3.1.2.1.28.

12. The method of claim 1, wherein the trehalase is an acid trehalase.

13. The method of claim 1, wherein the trehalase is a neutral trehalase.

14. The method of claim 1, wherein the medium comprises trehalose.

15. The method of claim 1, wherein the medium comprises starch.

16. The method of claim 15, wherein the starch is provided in a gelatinized or a raw form.

17. The method of claim 1, wherein the medium is derived from corn.

* * * * *